(12) United States Patent
Jimenez et al.

(10) Patent No.: US 8,932,302 B2
(45) Date of Patent: Jan. 13, 2015

(54) METHODS AND APPARATUS FOR INSERTION OF VERTEBRAL BODY DISTRACTION AND FUSION DEVICES

(71) Applicant: SpineX Tec LLC, Gering, NE (US)

(72) Inventors: Omar F. Jimenez, Gering, NE (US); Yefim I. Safris, Golden Valley, MN (US)

(73) Assignee: SpineX Tec, LLC, Gering, NE (US)

( * ) Notice: Subject to any disclaimer, the term of this patent is extended or adjusted under 35 U.S.C. 154(b) by 75 days.

(21) Appl. No.: 13/661,534

(22) Filed: Oct. 26, 2012

(65) Prior Publication Data

US 2013/0053966 A1     Feb. 28, 2013

Related U.S. Application Data

(63) Continuation-in-part of application No. 13/189,410, filed on Jul. 22, 2011, now Pat. No. 8,636,746.

(51) Int. Cl.
*A61B 17/58* (2006.01)
*A61B 17/60* (2006.01)
(Continued)

(52) U.S. Cl.
CPC ....... *A61F 2/447* (2013.01); *A61F 2002/30485* (2013.01); *A61F 2002/4475* (2013.01); *A61F*
(Continued)

(58) Field of Classification Search
USPC .......................... 606/99, 100, 105; 623/17.15
See application file for complete search history.

(56) References Cited

U.S. PATENT DOCUMENTS 2,106,088 A   1/1938   De Tar
2,231,221 A   2/1941   Rector
(Continued)

FOREIGN PATENT DOCUMENTS

EP   1342456    9/2003
EP   1881209    10/2008
(Continued)

OTHER PUBLICATIONS

Notification of Transmittal of the International Search Report and the Written Opinion of the International Searching Authority or the Declaration, Application No. PCT/US2010/042941, mailed Apr. 25, 2011.

(Continued)

*Primary Examiner* — Andrew Yang
(74) *Attorney, Agent, or Firm* — Patterson Thuente Pedersen, P.A.

(57) ABSTRACT

An inserter can be used to implant a distractible intervertebral body fusion device into a disc space and expand the device. The inserter includes a shaft frame and a drive shaft assembly for expanding the device and a support shaft assembly for stabilizing the device extending distally from the shaft frame. A drive housing can be operably connected to the shaft frame and extend outwardly from shaft frame distal of a proximal end of the shaft frame. Drive housing can have an internal passage that provides access into the shaft frame to a proximal end of the drive shaft assembly. An actuation tool can be disposed with the drive housing with a distal end extending through the access into the shaft frame to interface with the proximal end of the drive shaft assembly such that activation of the actuation tool rotates the drive shaft assembly to expand the device.

24 Claims, 39 Drawing Sheets

(51) Int. Cl.
  *A61F 2/00* (2006.01)
  *A61F 2/30* (2006.01)
  *A61F 2/44* (2006.01)
  *A61F 2/46* (2006.01)
  *A61F 2/48* (2006.01)

(52) U.S. Cl.
  CPC ....... 2002/30523 (2013.01); *A61F 2310/00029* (2013.01); *A61F 2002/30434* (2013.01); *A61F 2310/00017* (2013.01); *A61F 2002/4627* (2013.01); *A61F 2/4465* (2013.01); *A61F 2002/3063* (2013.01); *A61F 2310/00023* (2013.01); *A61F 2002/30092* (2013.01); *A61F 2002/4629* (2013.01); *A61F 2002/30525* (2013.01); *A61F 2002/4623* (2013.01); *A61F 2002/30285* (2013.01); *A61F 2/4611* (2013.01); *A61F 2002/30828* (2013.01); *A61F 2002/30556* (2013.01); *A61F 2002/4638* (2013.01); *A61F 2002/482* (2013.01); *A61F 2002/30405* (2013.01); *A61F 2002/30509* (2013.01); *A61F 2002/4662* (2013.01); *A61F 2002/30579* (2013.01); *A61F 2002/30601* (2013.01)
  USPC .......................... 606/99; 606/105; 623/17.15

(56) References Cited

U.S. PATENT DOCUMENTS

| | | |
|---|---|---|
| 2,453,656 A | 11/1948 | Bullard |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski |
| 3,700,290 A | 10/1972 | Ensinger |
| 3,708,925 A | 1/1973 | Ainoura |
| 3,709,132 A | 1/1973 | Farrell |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,103 A | 10/1984 | Benjamin |
| 4,516,303 A | 5/1985 | Kloster |
| 4,528,864 A | 7/1985 | Craig |
| 4,559,717 A | 12/1985 | Scire |
| 4,630,495 A | 12/1986 | Smith |
| 4,691,586 A | 9/1987 | Van Leijenhorst |
| 4,694,703 A | 9/1987 | Routson |
| 4,869,552 A | 9/1989 | Tolleson |
| 5,133,108 A | 7/1992 | Esnault |
| 5,181,371 A | 1/1993 | Deworth |
| 5,196,857 A | 3/1993 | Chiappetta |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett |
| 5,439,377 A | 8/1995 | Milanovich |
| 5,445,471 A | 8/1995 | Wexler |
| 5,645,599 A | 7/1997 | Samani |
| 5,664,457 A | 9/1997 | Nejati |
| 5,904,479 A | 5/1999 | Staples |
| 5,960,670 A | 10/1999 | Iverson |
| 5,980,252 A | 11/1999 | Samchukov |
| 5,988,006 A | 11/1999 | Fleytman |
| 6,045,579 A | 4/2000 | Hochshuler |
| 6,056,491 A | 5/2000 | Hsu |
| 6,136,031 A | 10/2000 | Middleton |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina |
| 6,454,806 B1 | 9/2002 | Cohen |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet |
| 6,641,614 B1 | 11/2003 | Wagner |
| 6,719,796 B2 | 4/2004 | Cohen |
| 6,752,832 B2 | 6/2004 | Neumann |
| 6,772,479 B2 | 8/2004 | Hinkley |
| 6,802,229 B1 | 10/2004 | Lambert |
| 6,808,537 B2 | 10/2004 | Michelson |
| 6,863,673 B2 | 3/2005 | Gerbec |
| 6,932,844 B2 | 8/2005 | Ralph |
| 6,953,477 B2 | 10/2005 | Berry |
| 7,018,415 B1 | 3/2006 | McKay |
| 7,051,610 B2 | 5/2006 | Stoianovici |
| 7,070,598 B2 | 7/2006 | Lim |
| 7,201,751 B2 | 4/2007 | Zucherman |
| 7,273,373 B2 | 9/2007 | Horiuchi |
| 7,308,747 B2 | 12/2007 | Smith |
| 7,316,381 B2 | 1/2008 | Hacker |
| 7,410,201 B1 | 8/2008 | Wilson |
| 7,425,103 B2 | 9/2008 | Perez-Sanchez |
| 7,435,032 B1 | 10/2008 | Murphey |
| 7,584,682 B2 | 9/2009 | Hsiao |
| 7,611,538 B2 | 11/2009 | Belliard |
| 7,632,281 B2 | 12/2009 | Errico |
| 7,674,296 B2 | 3/2010 | Rhoda |
| 7,682,376 B2 | 3/2010 | Trieu |
| 7,708,779 B2 | 5/2010 | Edie |
| 7,712,389 B2 | 5/2010 | Wang |
| 7,753,958 B2 | 7/2010 | Gordon |
| 7,758,645 B2 | 7/2010 | Studer |
| 7,758,648 B2 | 7/2010 | Castleman |
| 7,892,285 B2 | 2/2011 | Viker |
| 7,896,919 B2 | 3/2011 | Belliard |
| 7,947,078 B2 | 5/2011 | Siegal |
| 7,985,256 B2 | 7/2011 | Grotz |
| 8,070,813 B2 | 12/2011 | Grotz |
| 8,088,163 B1 | 1/2012 | Kleiner |
| 8,192,495 B2 | 6/2012 | Simpson |
| 8,303,663 B2 | 11/2012 | Jimenez et al. |
| 8,523,944 B2 | 9/2013 | Jimenez et al. |
| 2003/0077110 A1 | 4/2003 | Knowles |
| 2003/0233145 A1 | 12/2003 | Landry |
| 2004/0111157 A1 | 6/2004 | Ralph |
| 2004/0225364 A1 | 11/2004 | Richelsoph et al. |
| 2005/0000228 A1 | 1/2005 | De Sousa |
| 2005/0033431 A1 | 2/2005 | Gordon |
| 2005/0095384 A1 | 5/2005 | Wittmeyer |
| 2005/0113924 A1 | 5/2005 | Buttermann |
| 2005/0175406 A1 | 8/2005 | Perez-Sanchez |
| 2006/0004447 A1 | 1/2006 | Mastrorio |
| 2006/0004455 A1 | 1/2006 | Leonard |
| 2006/0025862 A1 | 2/2006 | Villiers |
| 2006/0129244 A1 | 6/2006 | Ensign |
| 2006/0149385 A1 | 7/2006 | McKay |
| 2006/0184171 A1 | 8/2006 | Biedermann |
| 2006/0247781 A1 | 11/2006 | Francis |
| 2006/0293752 A1 | 12/2006 | Moumene |
| 2007/0049943 A1 | 3/2007 | Moskowitz |
| 2007/0083267 A1 | 4/2007 | Miz |
| 2007/0129730 A1 | 6/2007 | Woods et al. |
| 2007/0185577 A1 | 8/2007 | Malek |
| 2007/0191954 A1 | 8/2007 | Hansell |
| 2007/0191958 A1 | 8/2007 | Abdou |
| 2007/0198089 A1 | 8/2007 | Moskowitz |
| 2007/0219634 A1 | 9/2007 | Greenhalgh |
| 2007/0222100 A1 | 9/2007 | Husted |
| 2007/0250171 A1 | 10/2007 | Bonin, Jr. |
| 2007/0255415 A1 | 11/2007 | Edie |
| 2007/0282449 A1 | 12/2007 | Villiers |
| 2007/0293329 A1 | 12/2007 | Glimpel |
| 2007/0293948 A1 | 12/2007 | Bagga |
| 2008/0026903 A1 | 1/2008 | Flugrad |
| 2008/0077246 A1 | 3/2008 | Fehling |

(56) References Cited

U.S. PATENT DOCUMENTS

| | | | |
|---|---|---|---|
| 2008/0091211 A1 | 4/2008 | Gately | |
| 2008/0100179 A1 | 5/2008 | Ruggeri | |
| 2008/0140207 A1* | 6/2008 | Olmos et al. | 623/17.16 |
| 2008/0147194 A1 | 6/2008 | Grotz | |
| 2008/0161920 A1 | 7/2008 | Melkent | |
| 2008/0161931 A1 | 7/2008 | Perez-Cruet | |
| 2008/0168855 A1 | 7/2008 | Giefer | |
| 2008/0188941 A1 | 8/2008 | Grotz | |
| 2008/0210039 A1 | 9/2008 | Brun | |
| 2008/0221694 A1 | 9/2008 | Warnick | |
| 2008/0234736 A1 | 9/2008 | Trieu | |
| 2008/0281423 A1 | 11/2008 | Sheffer | |
| 2008/0292392 A1 | 11/2008 | Voellmer | |
| 2008/0319487 A1 | 12/2008 | Fielding | |
| 2009/0012564 A1 | 1/2009 | Chirico | |
| 2009/0076614 A1 | 3/2009 | Arramon | |
| 2009/0164017 A1 | 6/2009 | Sommerich | |
| 2009/0210061 A1 | 8/2009 | Sledge | |
| 2009/0222100 A1 | 9/2009 | Cipoletti | |
| 2009/0234362 A1 | 9/2009 | Blain et al. | |
| 2009/0306672 A1 | 12/2009 | Reindel et al. | |
| 2010/0004688 A1 | 1/2010 | Maas | |
| 2010/0076557 A1 | 3/2010 | Miller | |
| 2010/0082109 A1 | 4/2010 | Greenhalgh | |
| 2010/0094305 A1 | 4/2010 | Chang | |
| 2010/0185291 A1 | 7/2010 | Jimenez et al. | |
| 2010/0192715 A1 | 8/2010 | Vauchel et al. | |
| 2010/0209184 A1 | 8/2010 | Jimenez et al. | |
| 2011/0054616 A1 | 3/2011 | Kamran | |
| 2011/0093075 A1 | 4/2011 | Duplessis | |
| 2011/0112644 A1 | 5/2011 | Zilberstein | |
| 2011/0138948 A1 | 6/2011 | Jimenez et al. | |
| 2011/0160861 A1 | 6/2011 | Jimenez et al. | |
| 2011/0270398 A1 | 11/2011 | Grotz | |
| 2012/0116518 A1 | 5/2012 | Grotz | |
| 2012/0158071 A1 | 6/2012 | Jimenez et al. | |
| 2012/0323329 A1 | 12/2012 | Jimenez et al. | |

FOREIGN PATENT DOCUMENTS

| | | |
|---|---|---|
| FR | 2372998 A1 | 12/1976 |
| JP | 05-81194 | 11/1993 |
| JP | 2004-301135 | 10/2004 |
| JP | 2008-208932 | 9/2008 |
| WO | WO 2004/026188 | 4/2004 |
| WO | WO 2004/109155 | 12/2004 |
| WO | WO 2005/081330 | 9/2005 |
| WO | WO 2006/094535 | 9/2006 |
| WO | WO 2006/116052 | 11/2006 |
| WO | WO 2006/125329 | 11/2006 |
| WO | WO 2007/002583 | 1/2007 |
| WO | WO 2007/028140 | 3/2007 |
| WO | WO 2007/111979 | 10/2007 |
| WO | WO 2008/137192 | 11/2008 |
| WO | WO 2009/018349 | 2/2009 |
| WO | WO 2010/078520 | 12/2009 |

OTHER PUBLICATIONS

International Search Report, Application No. PCT/US2010/042915, mailed Apr. 22, 2011.

International Search Report and Written Opinion of the International Searching Authority or the Declaration dated Sep. 27, 2010, International Application No. PCT/US2009/069876, filed Dec. 30, 2009, 12 pages.

Wenzel Spine, Inc., *VariLift®-L Expandable Interbody Fusion Device: A proven solution for stand-alone fusion*, Product Overview, 12 pages, ® 2010.

Peter A. Halverson, et. al., Tension-based Multi-stable Compliant: Rolling-contact Elements, Department of Mechanical Engineering, Brigham Young University, Provo UT, USA 84602 (34 pages), 2007.

Just L. Herder, Force Directed Design of Laparoscopic Forceps, 1998, ASME Design Engineering Technical Conference (8 pages).

Alexander H. Slocum, Fundamentals of Design (2005).

Amelie Jeanneau, et. al., A Compliant Rolling Contact Joint and its Application in a 3-DOF Planar Parallel Mechanism with Kinematic Analysis, ASME (2004) Design Engineering Technical Conferences (9 pages).

International Search Report, mailed Jul. 14, 2011, Application No. PCT/US2009/069876, filed Dec. 30, 2009, 7 pages.

Application and File History of U.S. Appl. No. 12/650,994, Inventors Jimenez et al., filed Dec. 31, 2009.

Application and File History of U.S. Appl. No. 12/407,608, Inventors Omar F. Jimenez, filed Mar. 19, 2009.

Application and File History of U.S. Appl. No. 12/841,869, Inventors Jimenez et al., filed Jul. 22, 2010.

W. Kiisswetter, *A Supplementary Instrumentation for Posterior Fusion of Spine in Scoliosis*, Archives of Orthopedic Traumatic Surgery, 1980, 1 page.

Chou et al., *Efficacy of Anterior Cervical Fusion: Comparison of Titanium Cages, polyetheretherketone (PEEK) cages and autogenous bone grafts*, Journal of Clinical Neuroscience, 2008, pp. 1240-1245.

Hunter et al., *Overview of Medical Devices*, Department of Radiology, University of Arizona, Aug. 2001, pp. 89-140, vol. 30, No. 4, ISSN: 0363-0188.

Application and File History of U.S. Appl. No. 12/841,465, Inventors Jimenez et al., filed Jul. 22, 2010.

Application and File History of U.S. Appl. No. 13/591,463, filed Aug. 22, 2012, Inventors: Jimenez et al.

Application and File History for U.S. Appl. No. 13/189,410, Inventors: Jimenez et al, filed Jul. 22, 2011.

Medtronic Sofamor Danek USA, Inc., *CAPSTONE* Instrument Set Technique, http://www.mtortho.com/public/capstone.pdr, © 2005, 25 pages.

Medtronic, *CAPSTONE* PEEK Spinal System Surgical Technique, http://www.mtortho.com/public/capstone_peek_st.pdf. © 2009, 36 pages.

Japanese Application No. 2012-521784, JP Office Action dated Feb. 18, 2014, 8 pages.

PCT/US2013/067070, PCT Written Opinion/Search Report dated Feb. 27, 2014, 14 pages.

* cited by examiner

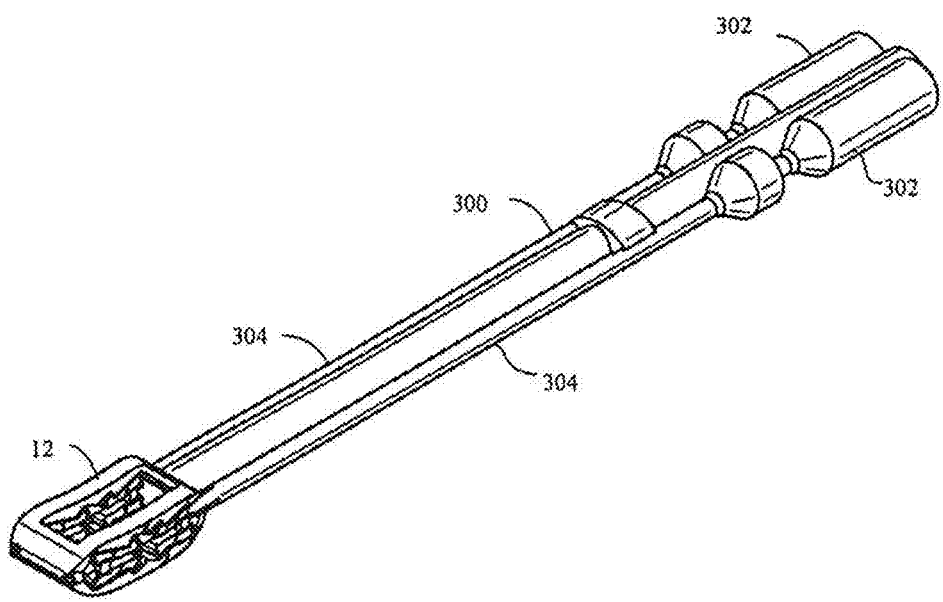

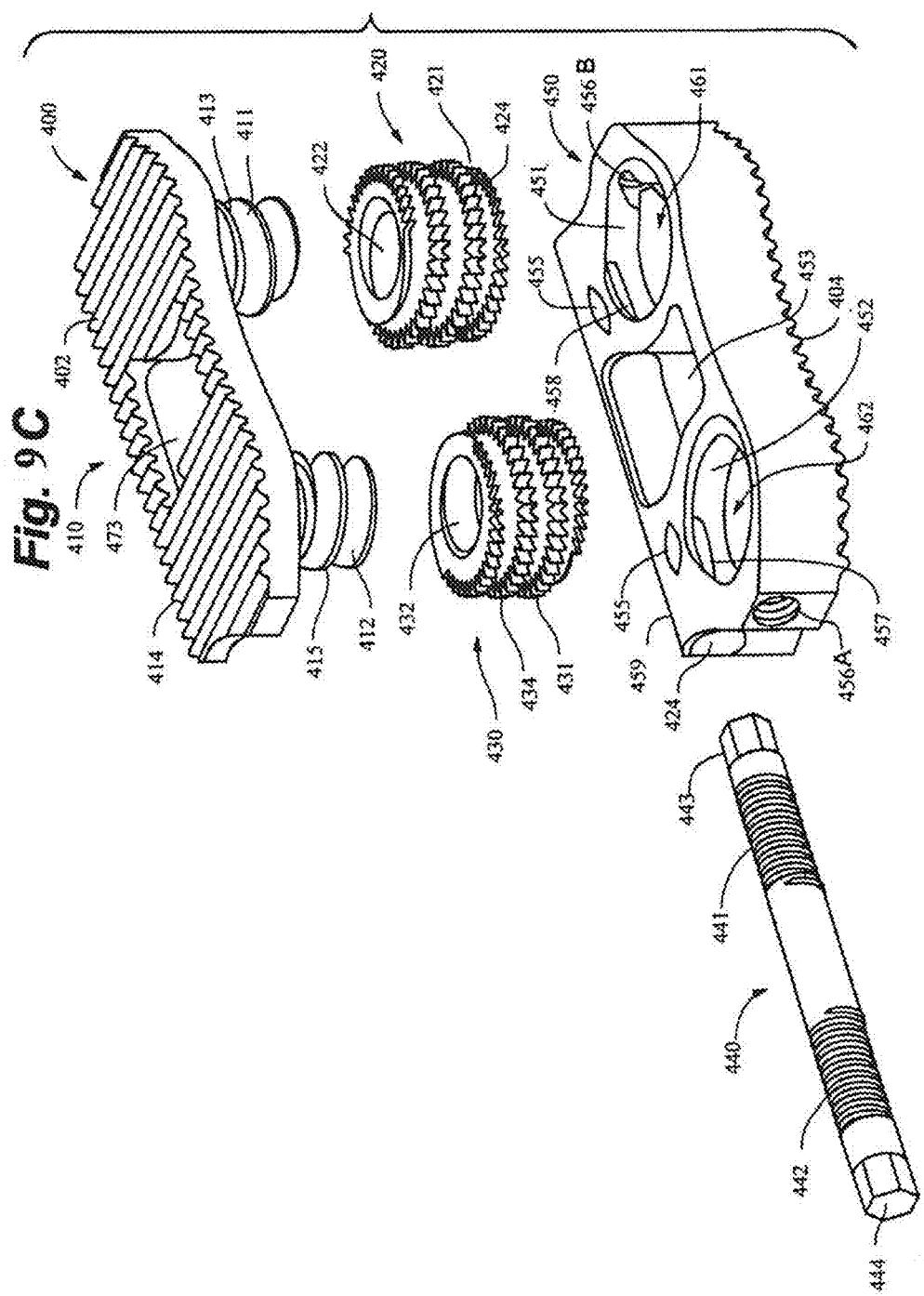

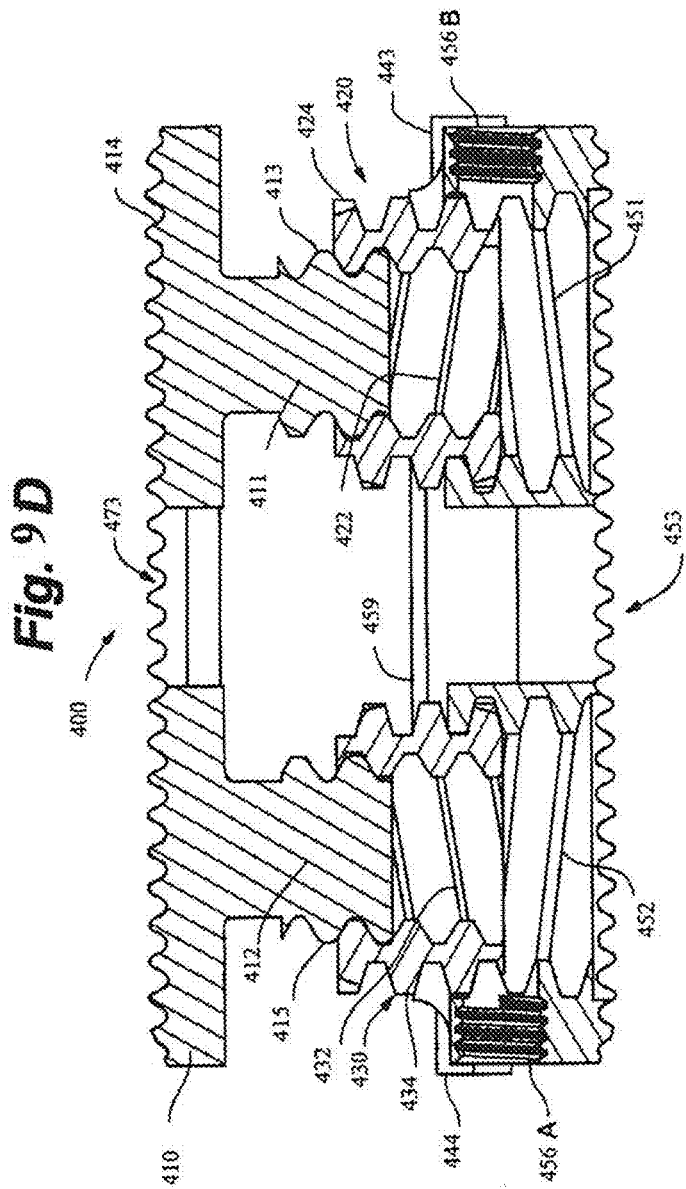

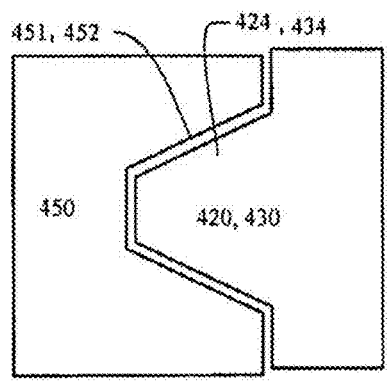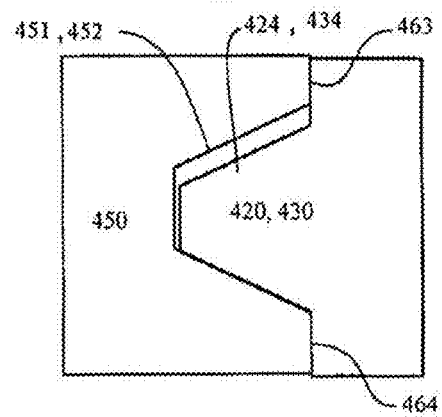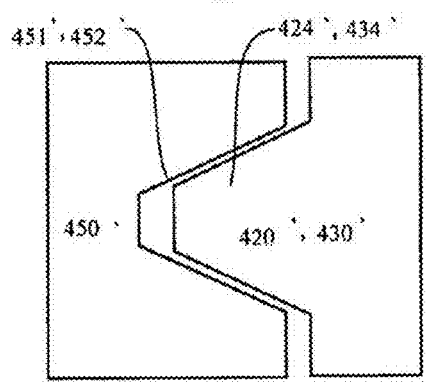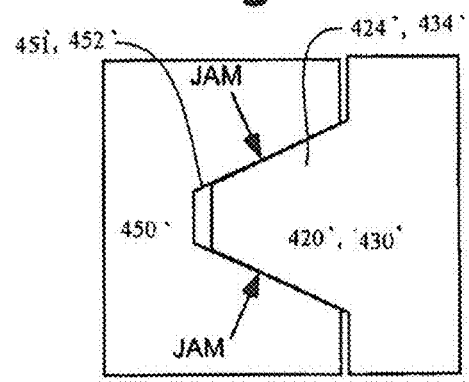

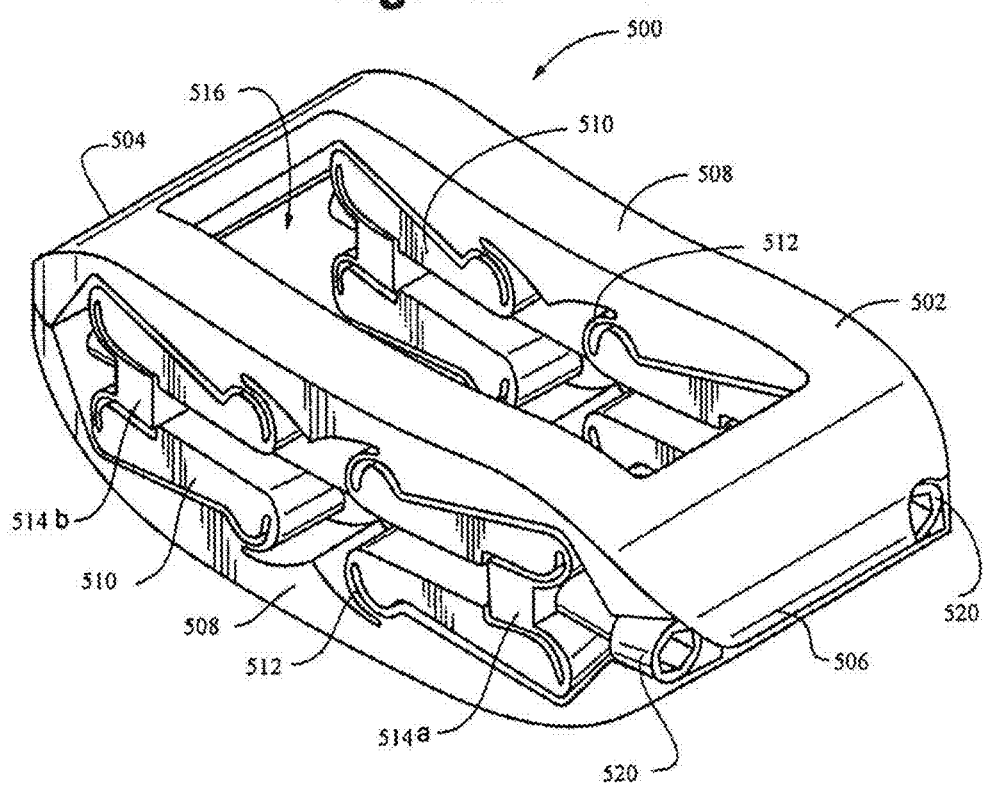

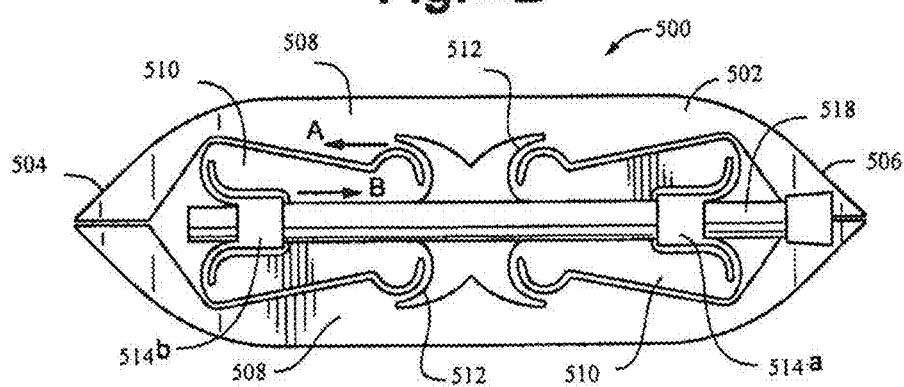

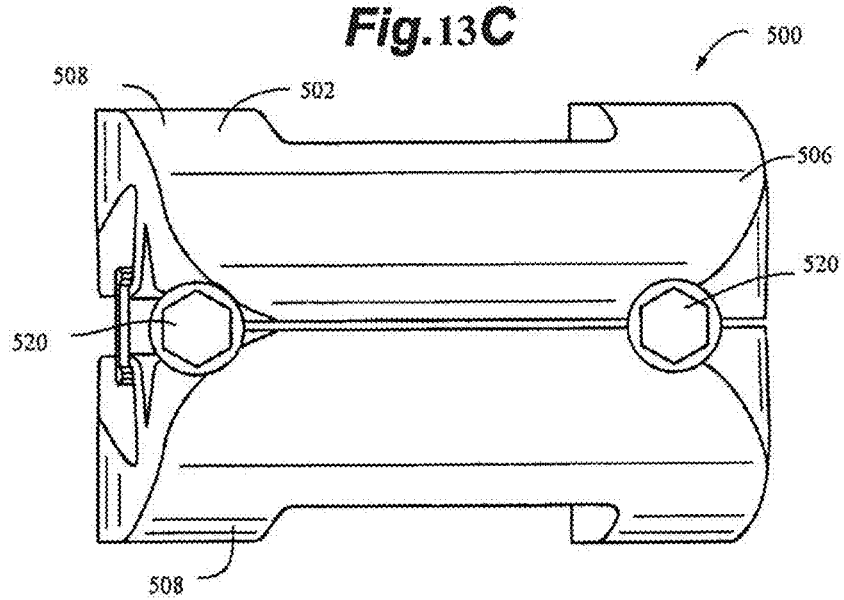

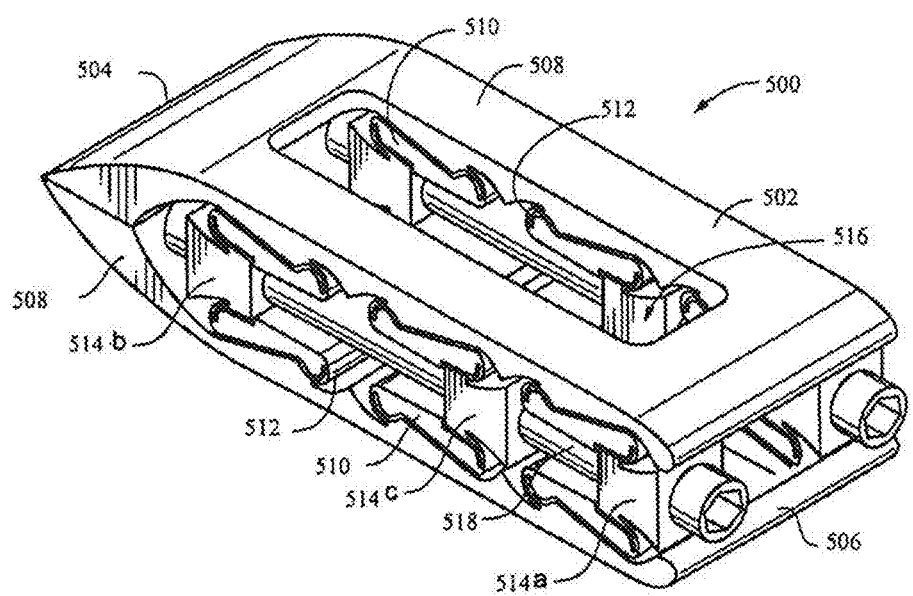

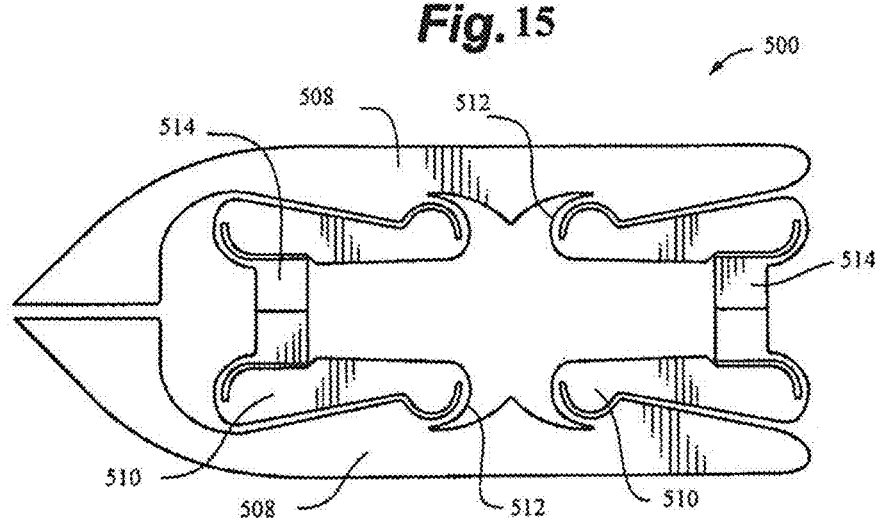

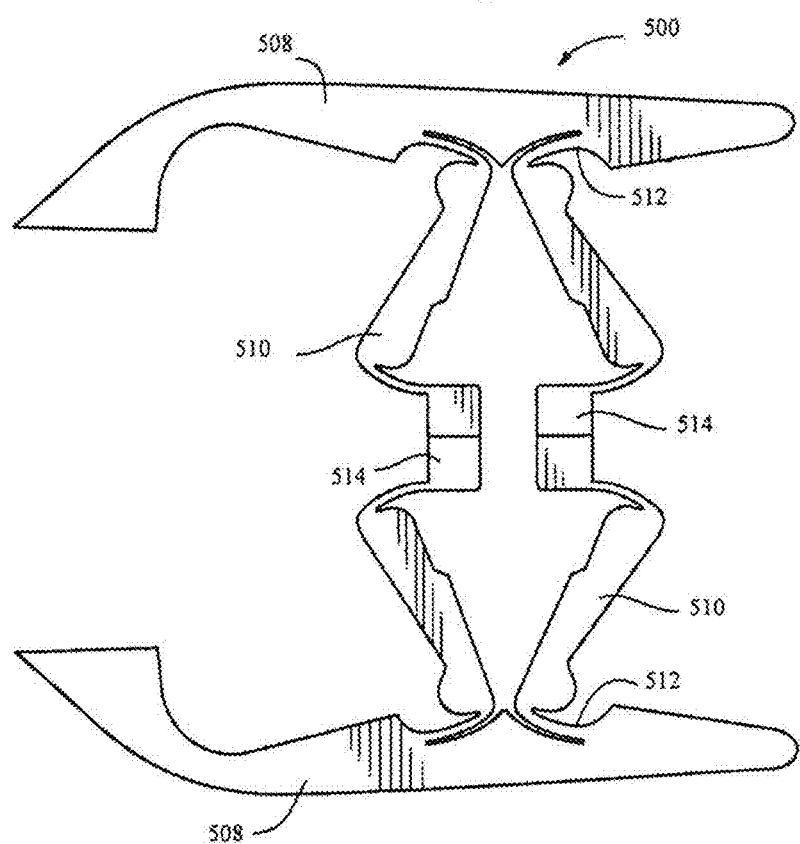

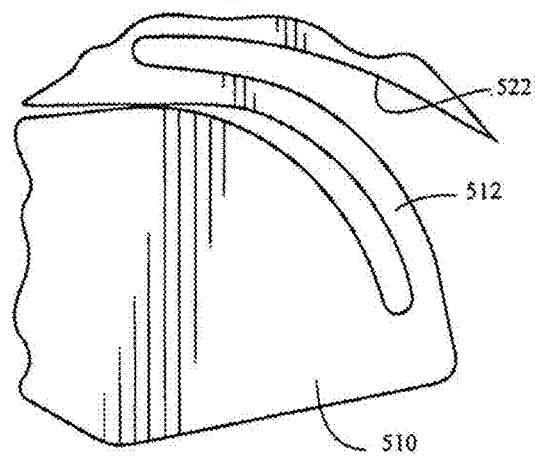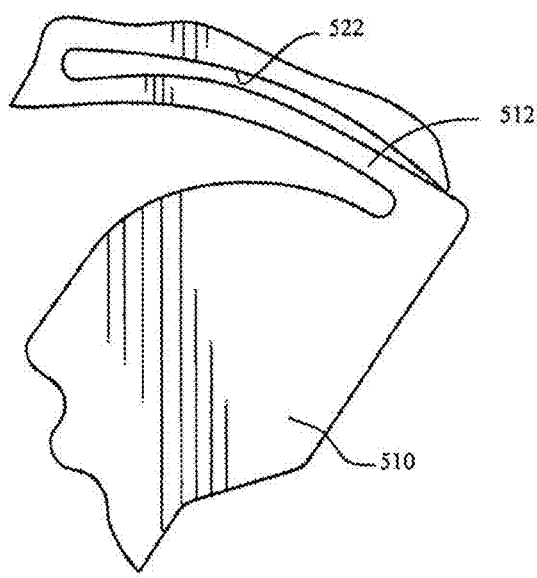

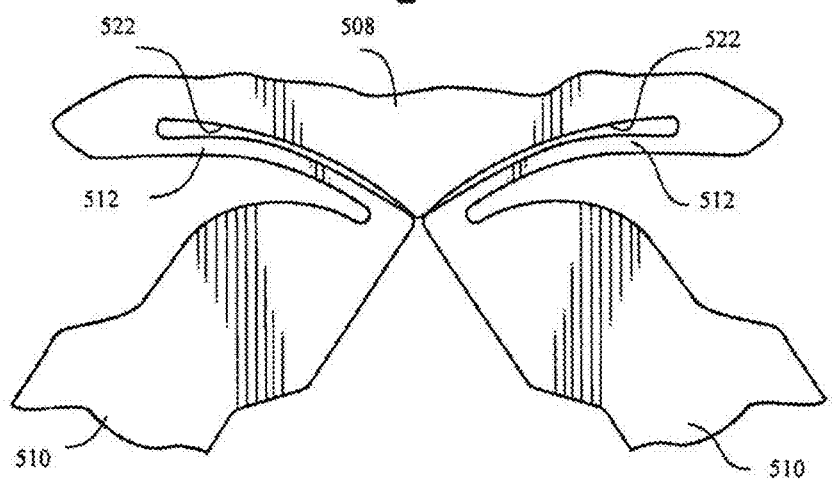

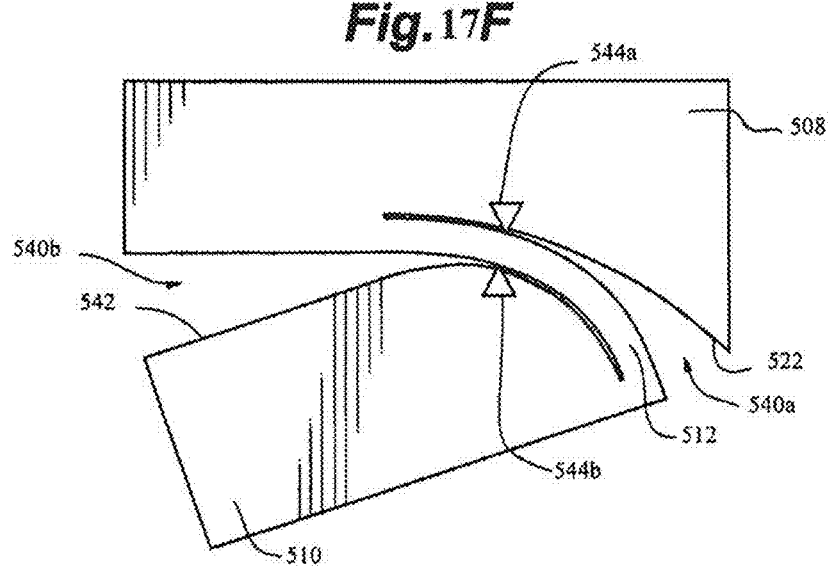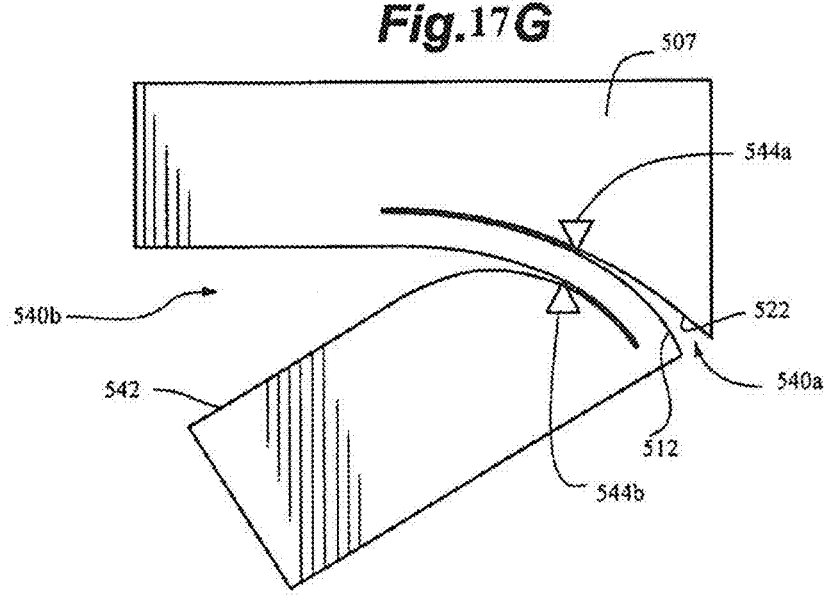

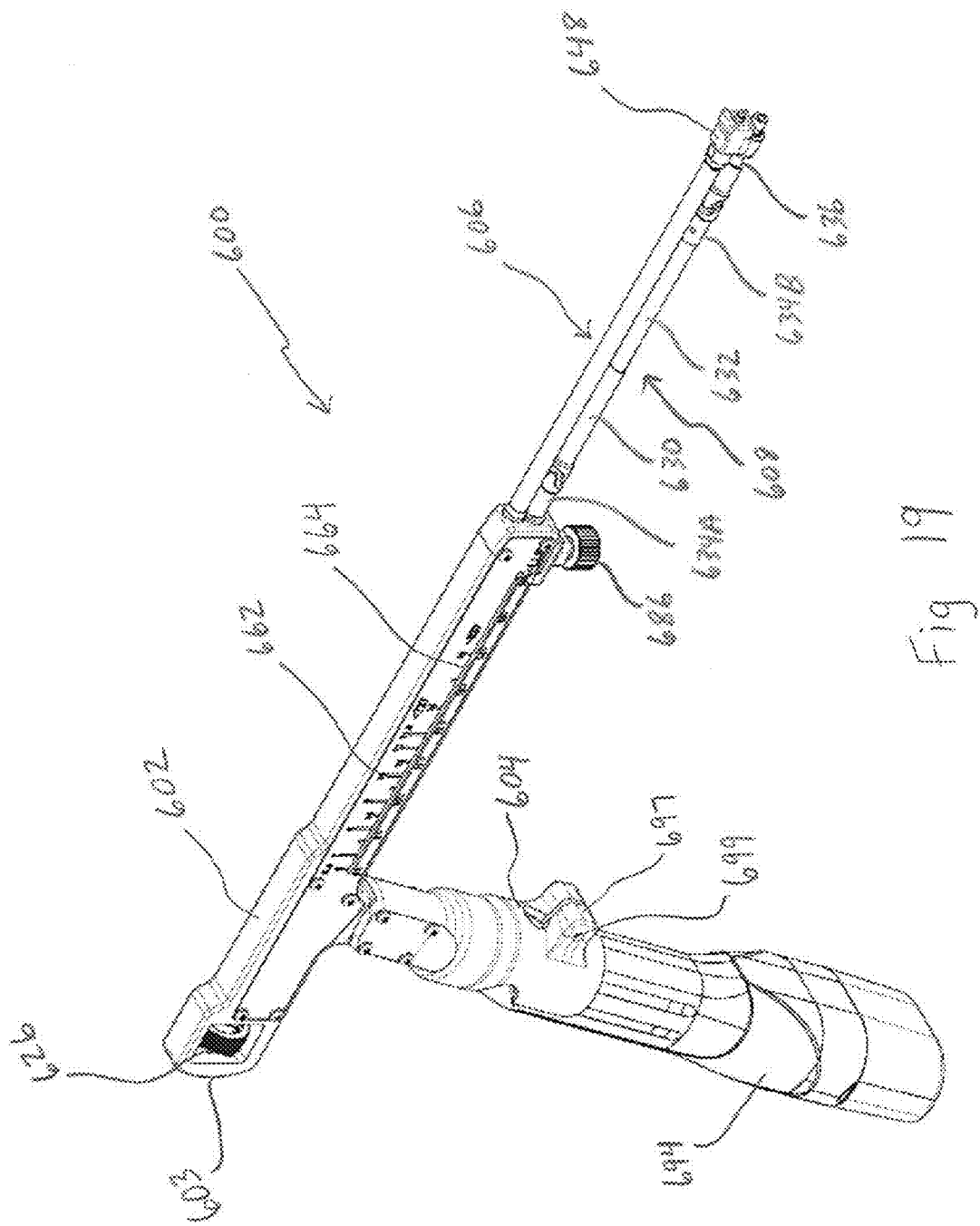

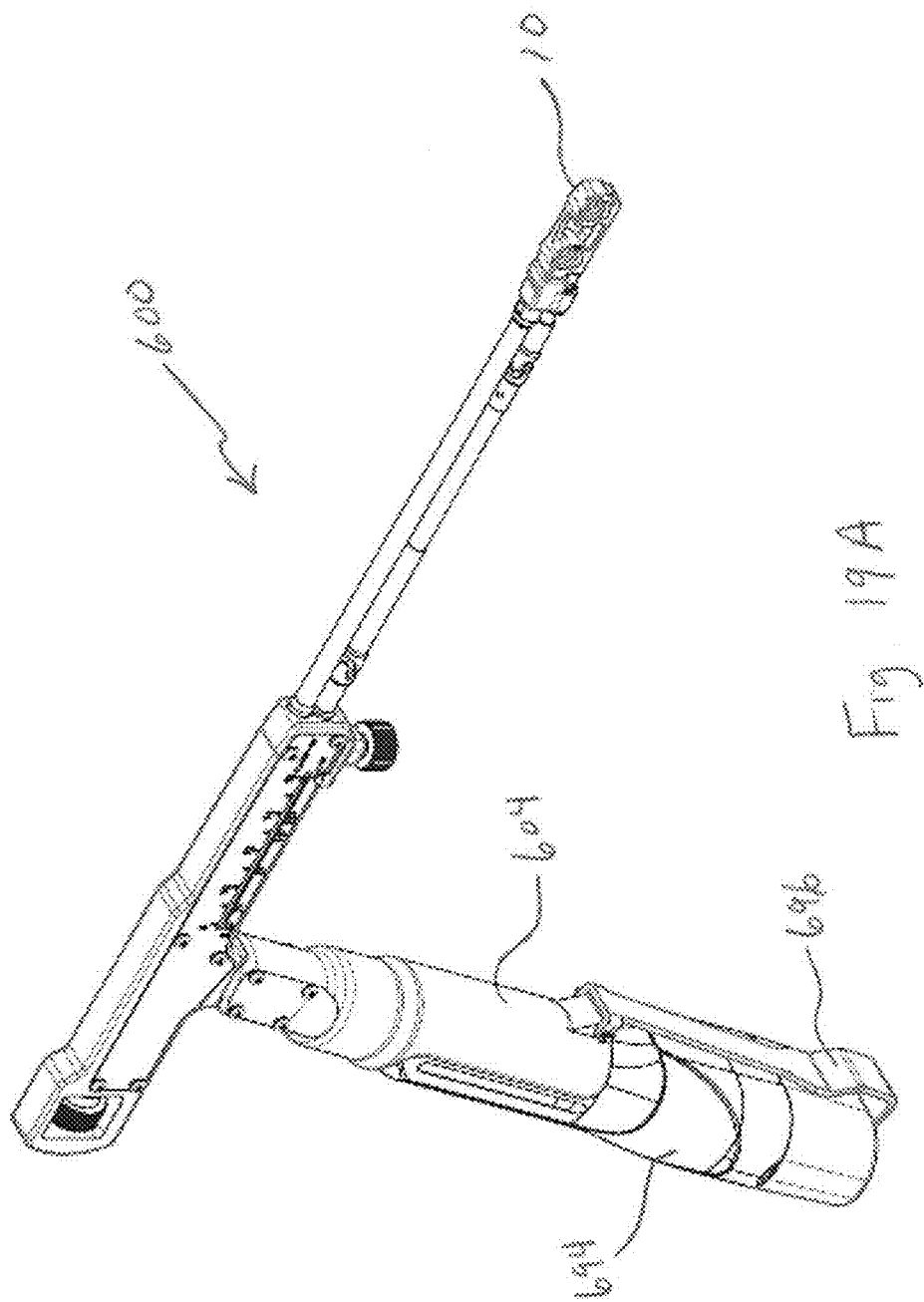

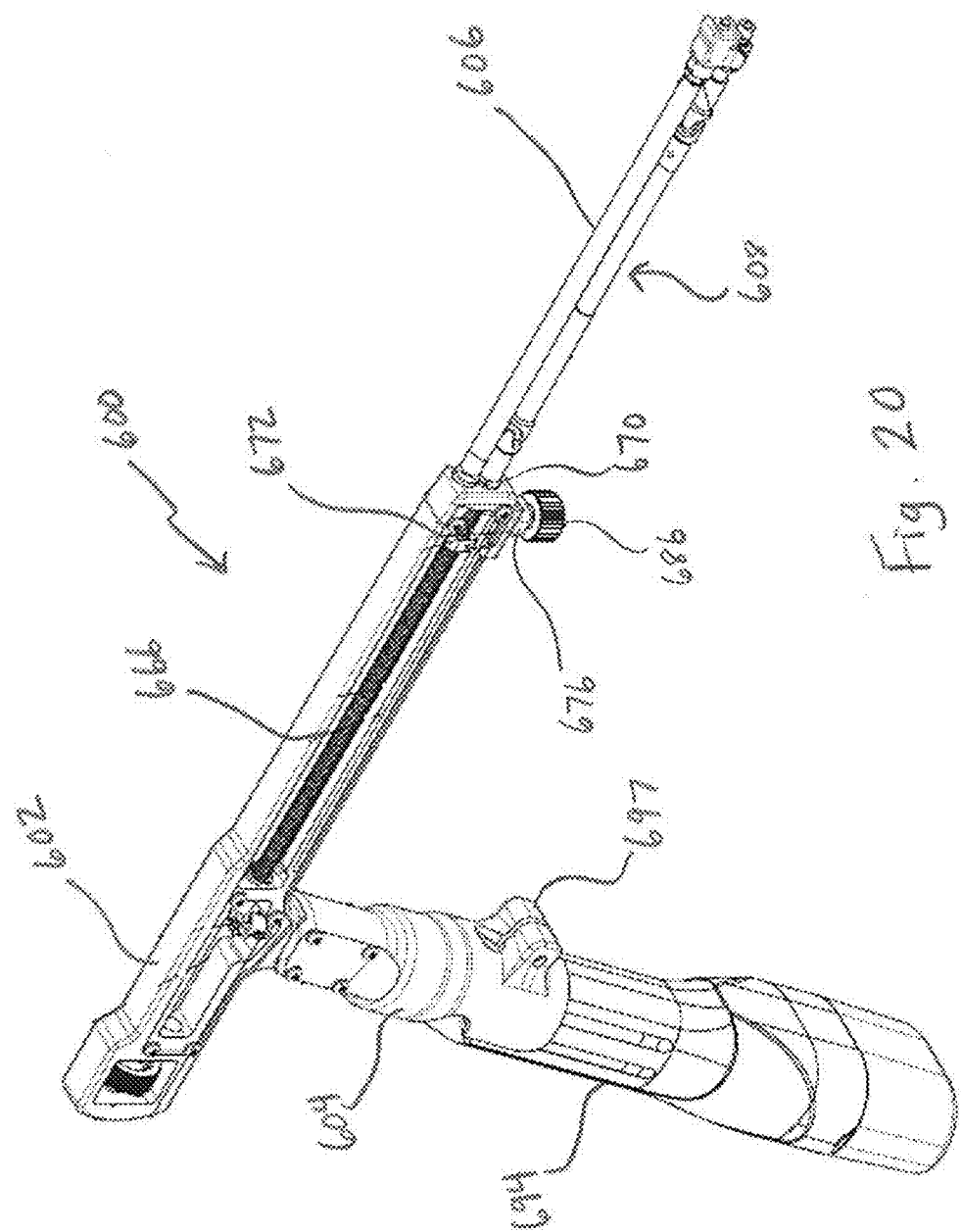

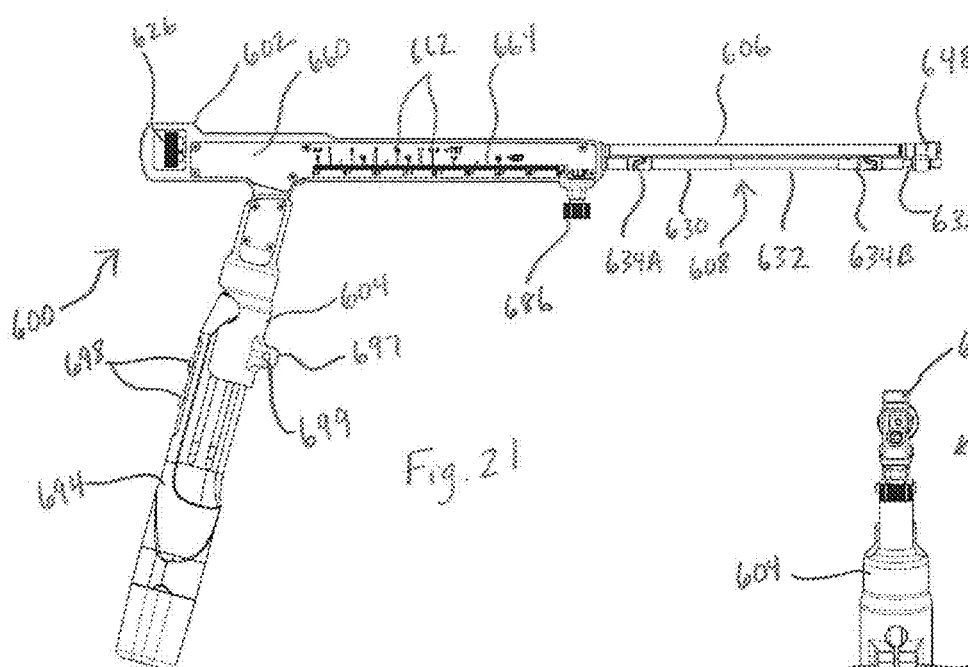
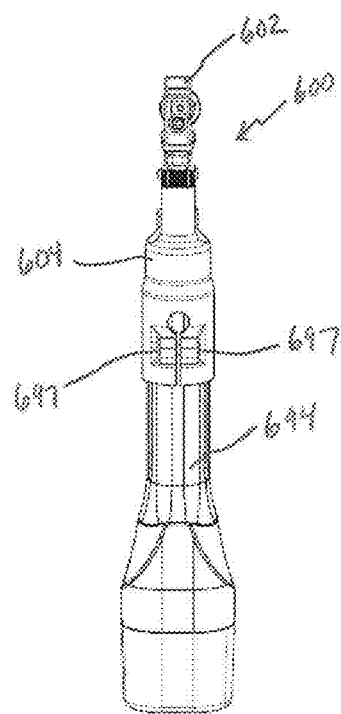
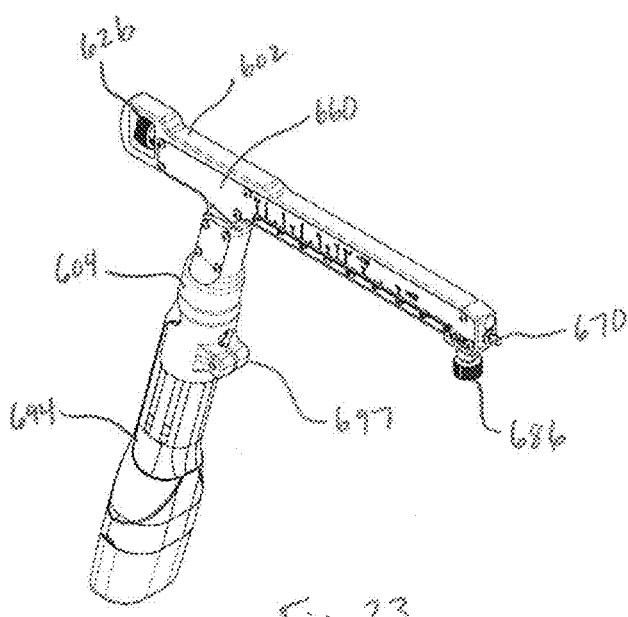

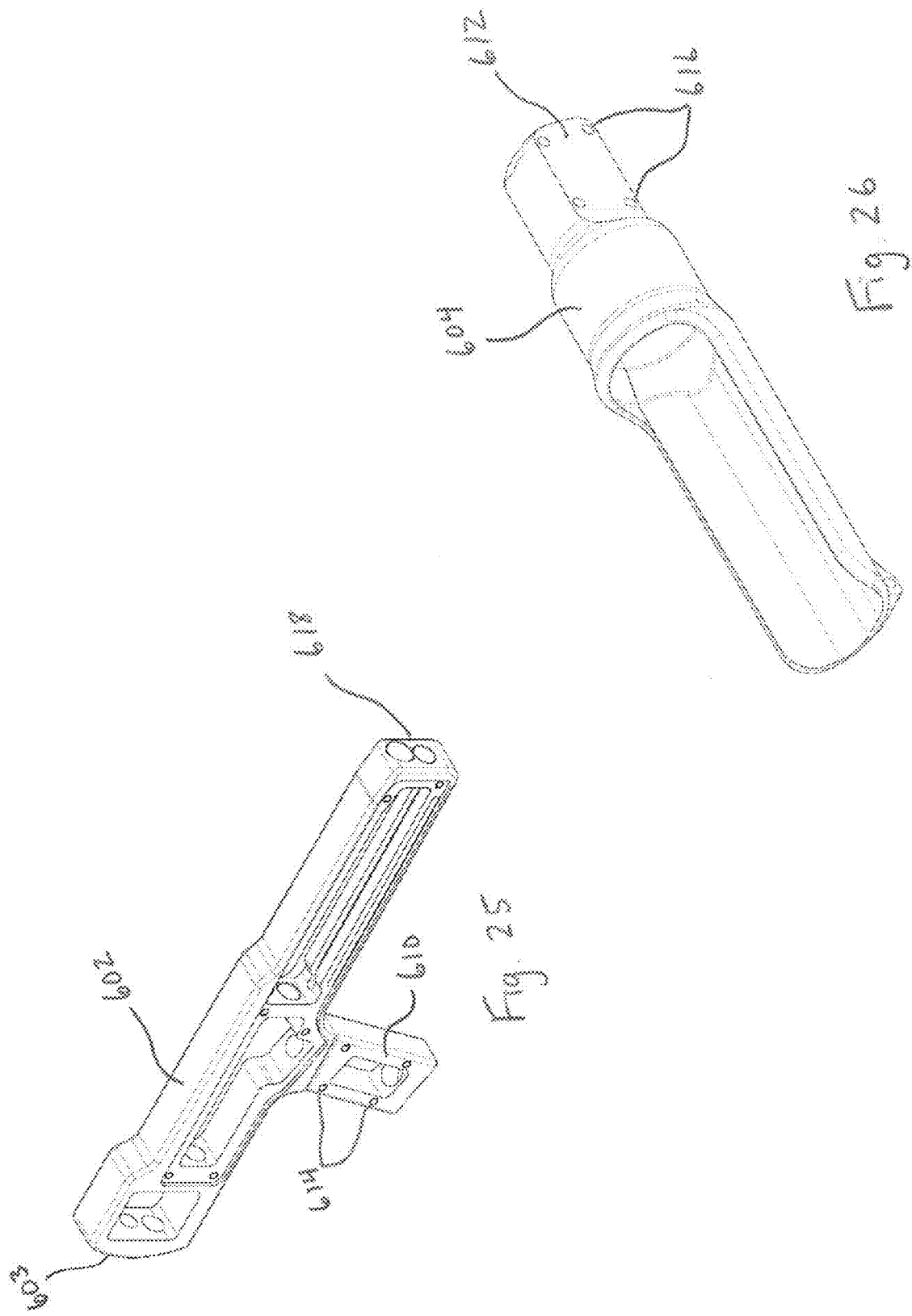

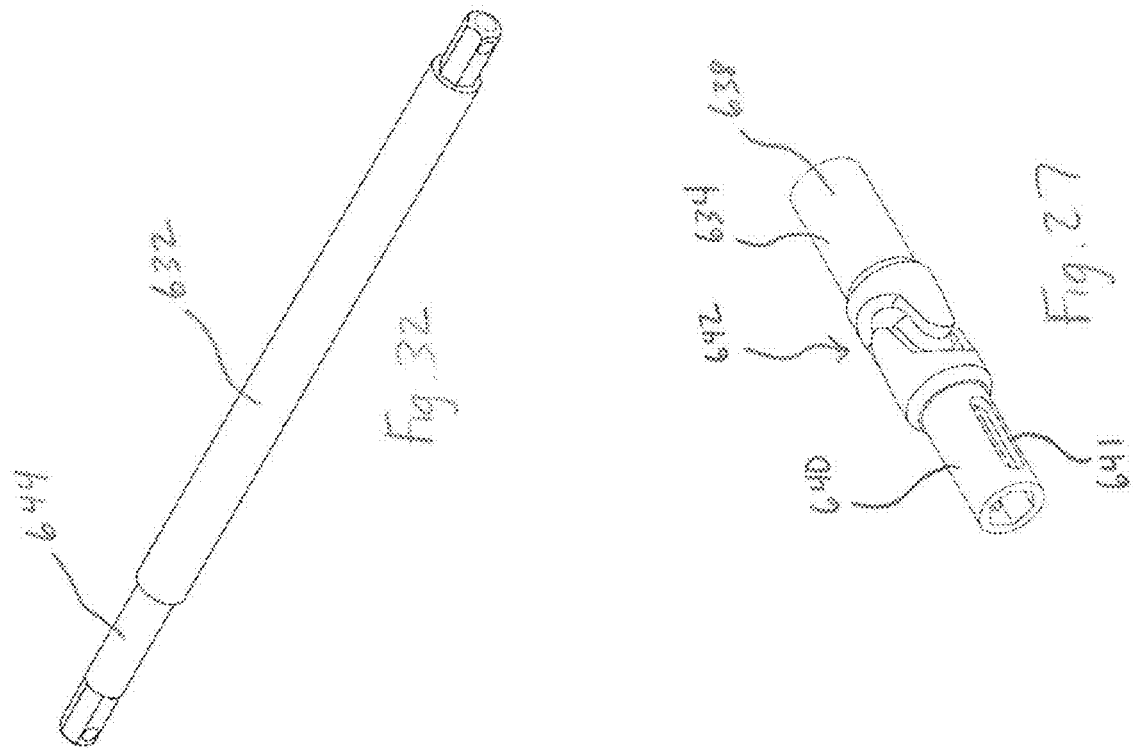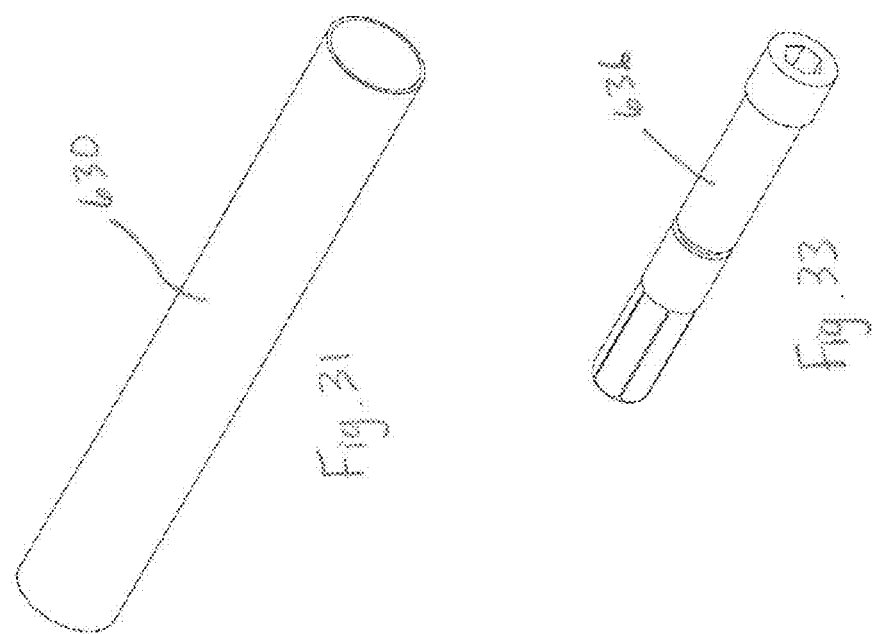

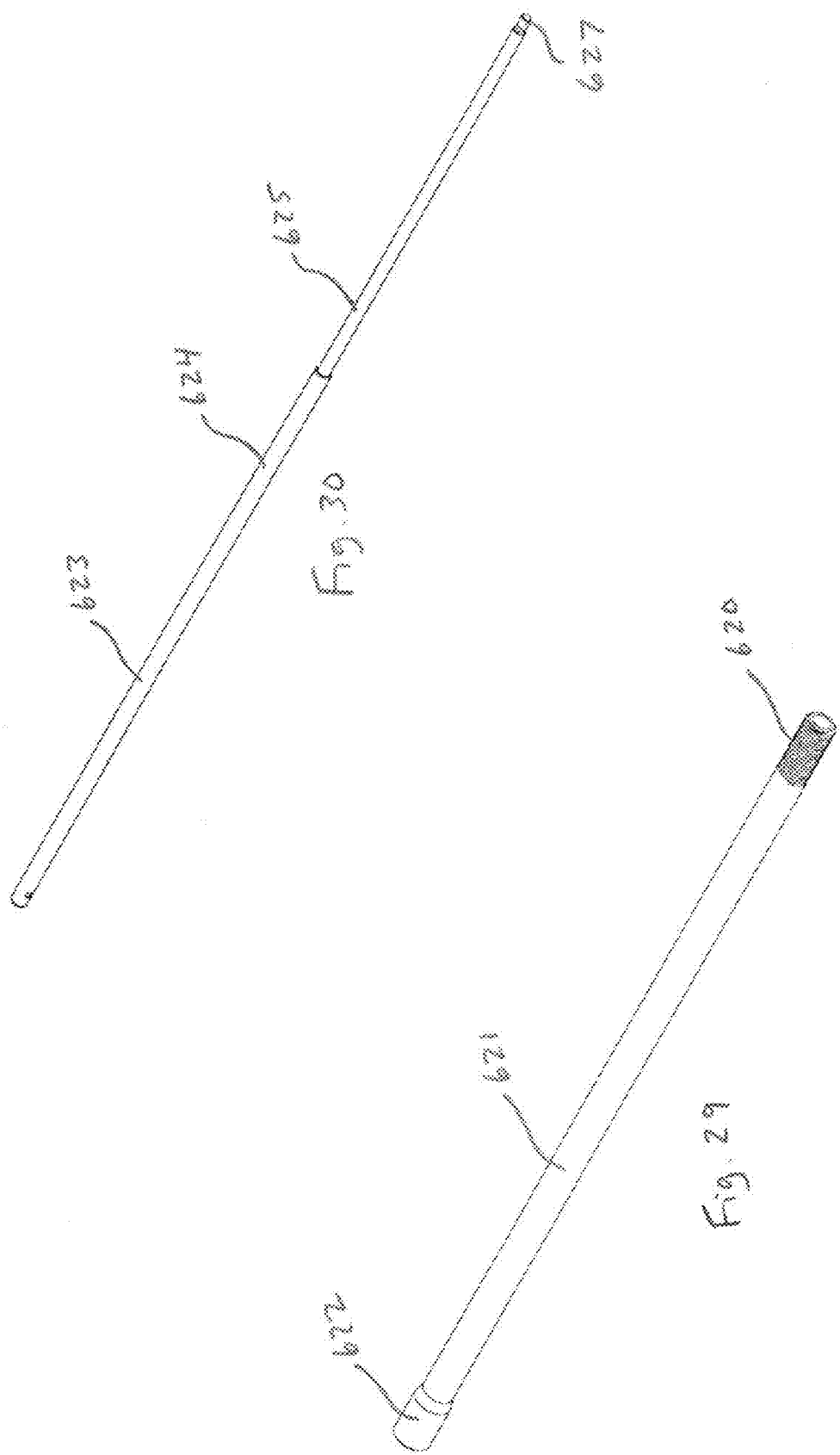

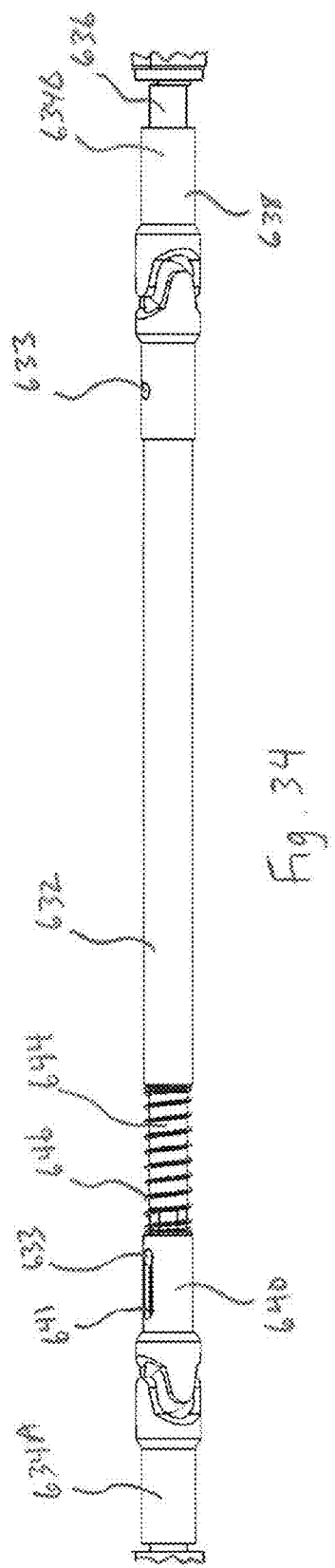

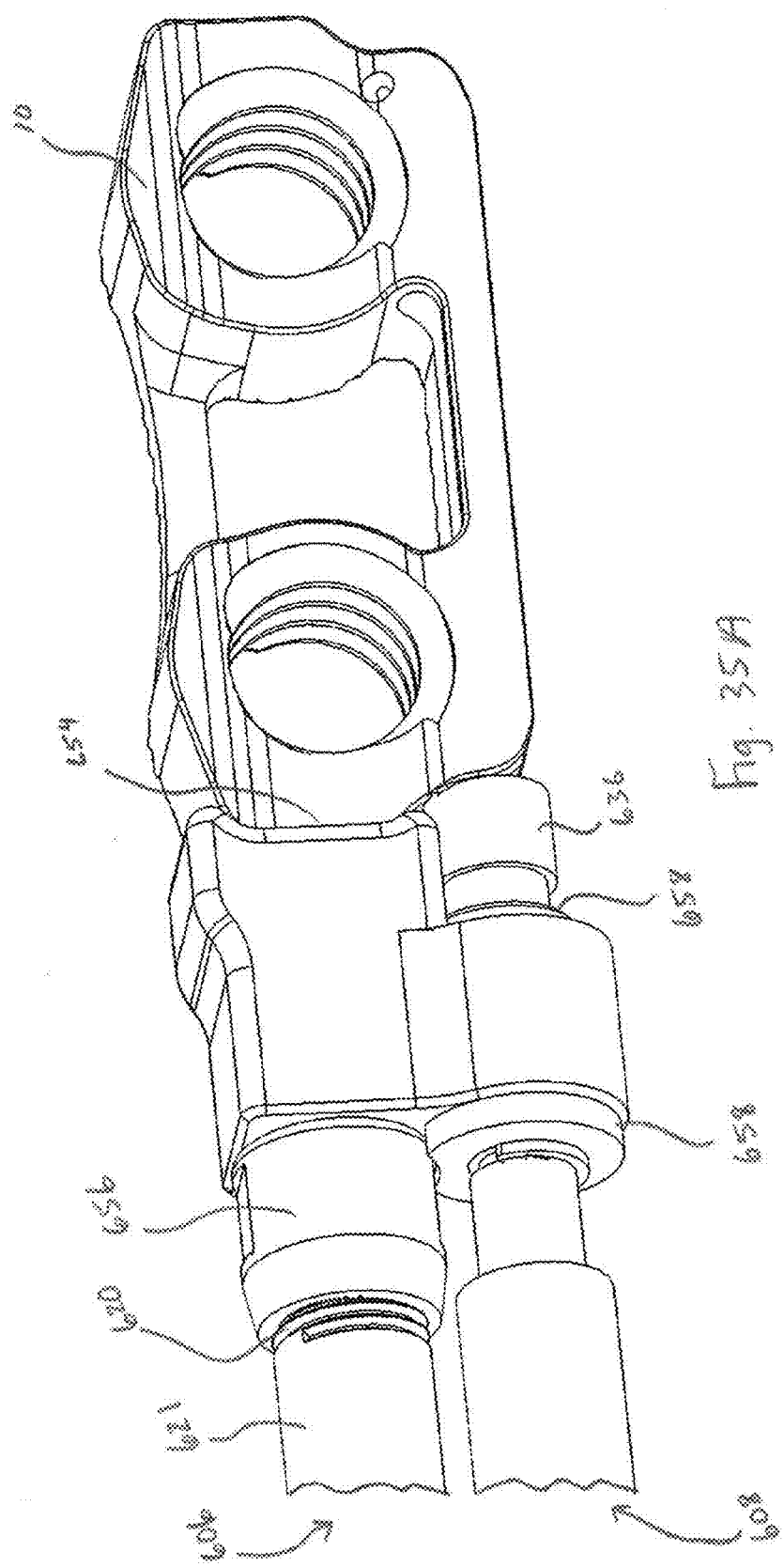

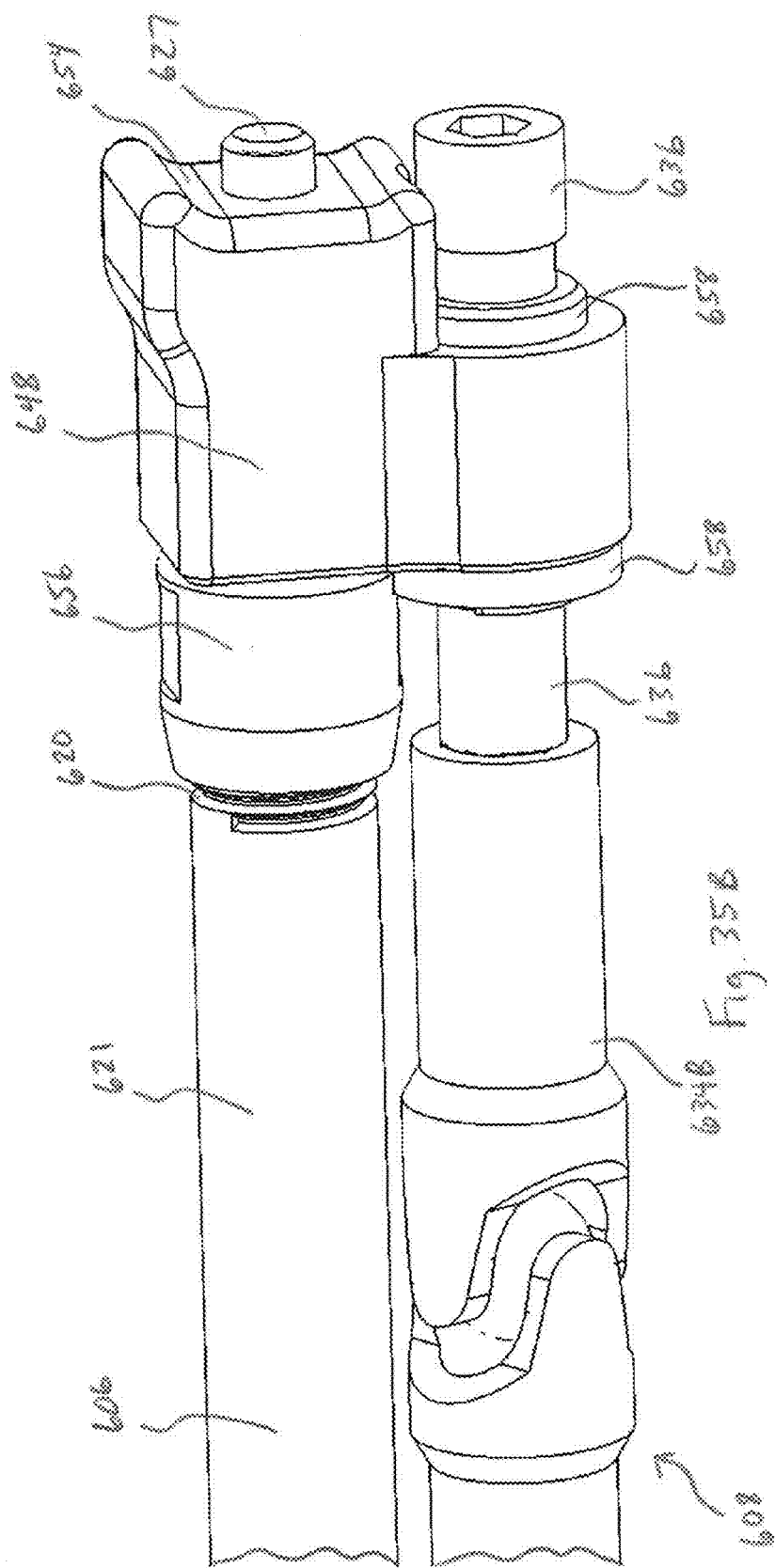

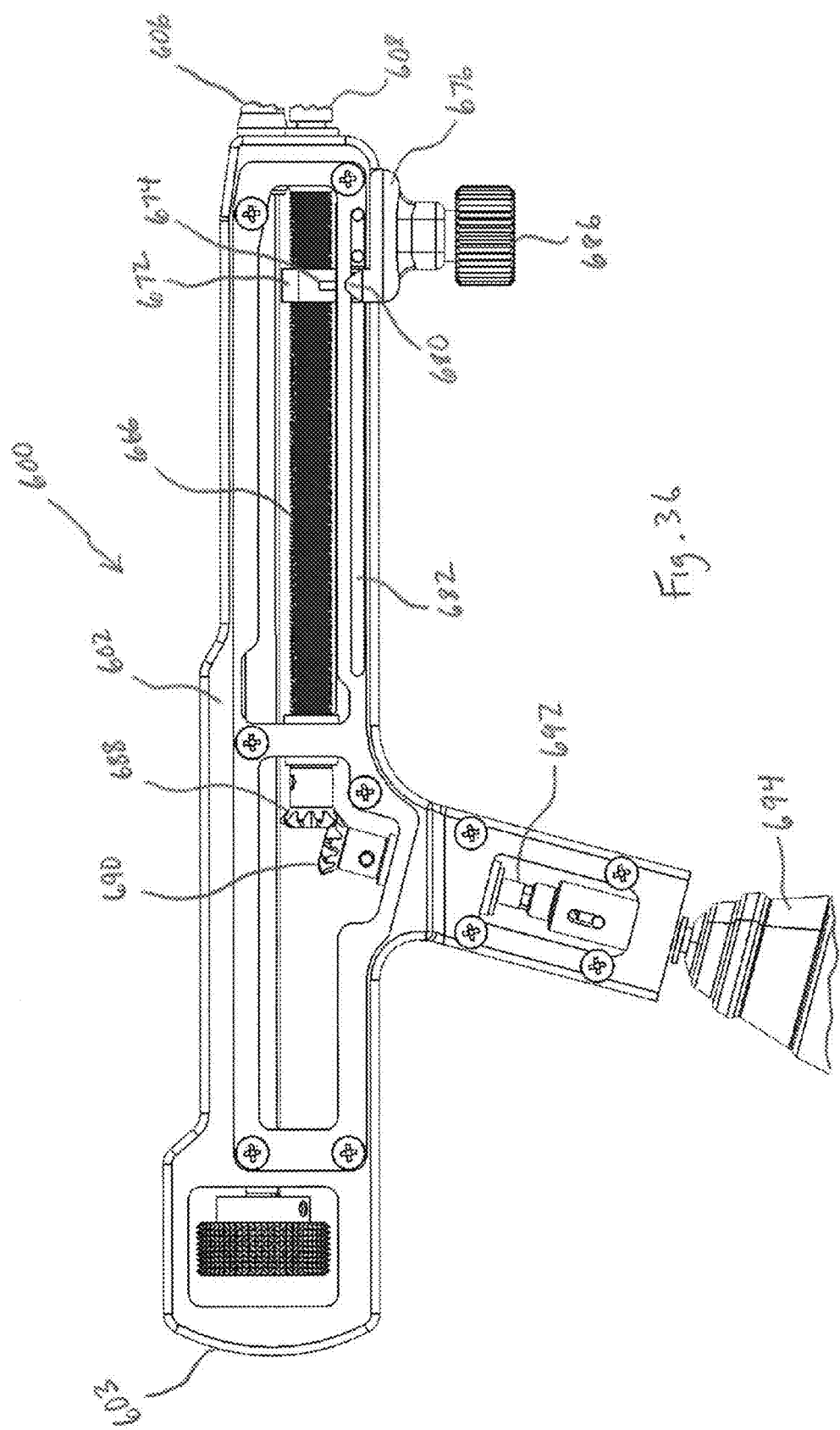

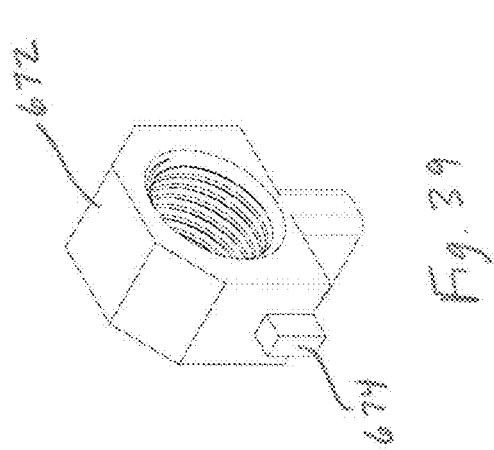
Fig. 39
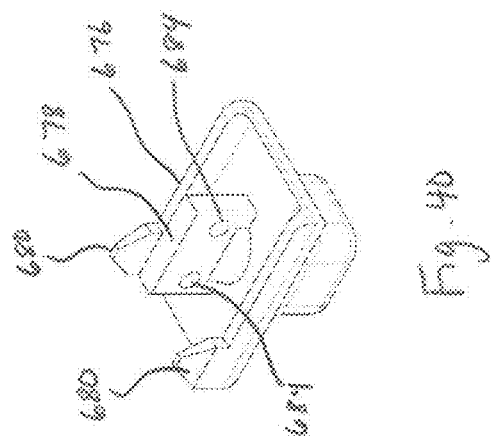
Fig. 40
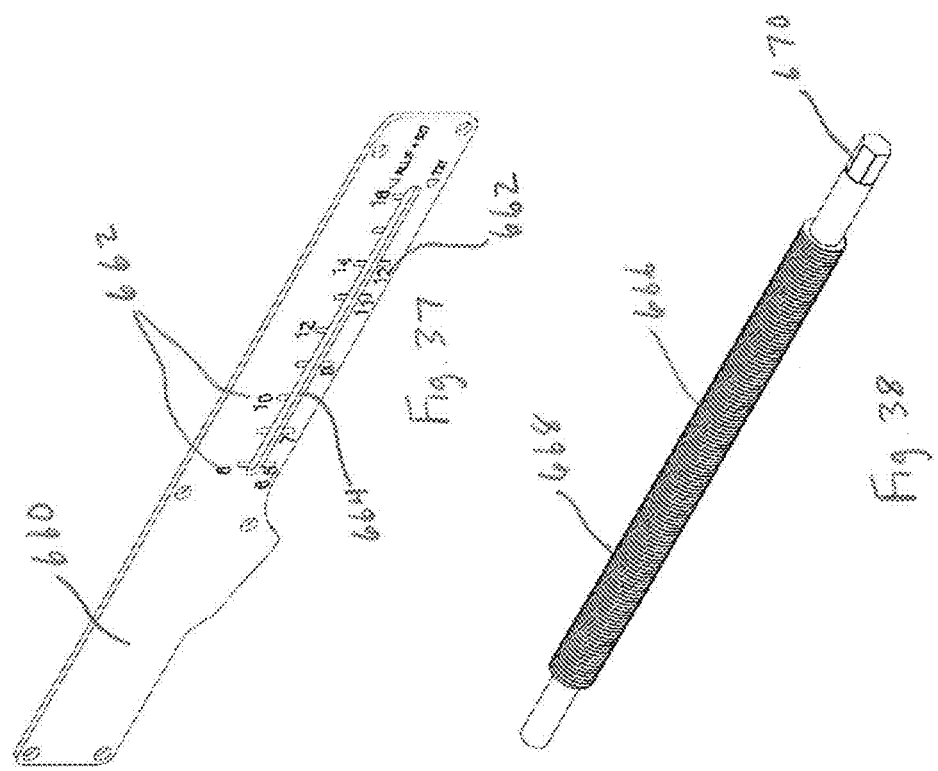
Fig. 37
Fig. 38

METHODS AND APPARATUS FOR INSERTION OF VERTEBRAL BODY DISTRACTION AND FUSION DEVICES

RELATED APPLICATION

This application is a continuation-in-part of application Ser. No. 13/189,410 filed Jul. 22, 2011, which is hereby fully incorporated herein by reference.

FIELD OF THE INVENTION

The present invention relates to the distraction and fusion of vertebral bodies. More specifically, the present invention relates to devices and methods for inserting and distracting vertebral fusion and distraction devices in the body.

BACKGROUND OF THE INVENTION

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root to allow load sharing to enhance bone formation, and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral fusion and distraction can be performed through anterior, posterior, oblique, and lateral approaches. Each approach has its own anatomic challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

Such devices need to be implanted into the disc space in a minimally invasive manner and then distracted to expand the disc space to the desired height. As such, a tool for implanting such devices that allows the distraction to be simply and accurately controlled is desirable.

SUMMARY OF THE INVENTION

An inserter can be used to implant a distractible intervertebral body fusion device into a patient's disc space and expand the device. The inserter can include a shaft frame and a drive shaft assembly for expanding the device and a support shaft assembly for stabilizing the device extending distally from the shaft frame. A drive housing can be operably connected to the shaft frame and extend outwardly from shaft frame at a point distal of a proximal end of the shaft frame. Drive housing can have an internal passage that provides access into the shaft frame to a proximal end of the drive shaft assembly. An actuation tool can be disposed with the drive housing, a distal end of which can extend through the access into the shaft frame to interface with the proximal end of the drive shaft assembly such that activation of the actuation tool rotates the drive shaft assembly to expand the device.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 7 is a perspective view of an introducer for inserting and distracting a distractible intervertebral body fusion device according to an embodiment of the present invention.

FIG. 9C is an exploded view of the distractible intervertebral body fusion device of FIG. 9A.

FIG. 9D is a partial sectional view of the distractible intervertebral body fusion device of FIG. 9A.

FIG. 10A is a partial side view of a distractible intervertebral body fusion device according to an embodiment of the present invention.

FIG. 10B is a partial side view of the distractible intervertebral body fusion device of FIG. 10A.

FIG. 11A is a partial side view of a distractible intervertebral body fusion device according to an embodiment of the present invention.

FIG. 11B is a partial side view of the distractible intervertebral body fusion device of FIG. 11A.

FIG. 13A is a perspective view of an embodiment of a distractible intervertebral body fusion device according to an aspect of the present invention.

FIG. 13B is a side view of the distractible intervertebral body fusion device of FIG. 13A.

FIG. 13C is an end view of the distractible intervertebral body fusion device of FIG. 13A.

FIG. 14A is a perspective view of an embodiment of a distractible intervertebral body fusion device according to an aspect of the present invention.

FIG. 15 is a side view of an embodiment of a distractible intervertebral body fusion device according to an aspect of the present invention.

FIG. 16 is a side view of an embodiment of a distractible intervertebral body fusion device according to an aspect of the present invention.

FIG. 17A is a partial view of a portion of an embodiment of a distractible intervertebral body fusion device according to an aspect of the present invention.

FIG. 17B is a partial view of a portion of an embodiment of a distractible intervertebral body fusion device according to an aspect of the present invention.

FIG. 17C is a partial view of a portion of an embodiment of a distractible intervertebral body fusion device according to an aspect of the present invention.

FIG. 17F is a partial view of a portion of an embodiment of a distractible intervertebral body fusion device according to an aspect of the present invention.

FIG. 17G is a partial view of a portion of an embodiment of a distractible intervertebral body fusion device according to an aspect of the present invention.

FIG. 19 is an isometric view of a device for inserting an intervertebral device according to an embodiment of the present invention;

FIG. 19A is an isometric view of a device for inserting an intervertebral device according to an embodiment of the present invention.

FIG. 20 is an isometric view of the device of FIG. 19;

FIG. 21 is a side view of the device of FIG. 19;

FIG. 22 is a rear view of the device of FIG. 19;

FIG. 23 is an isometric view of a portion of the device of FIG. 19;

FIG. 25 is an isometric view of a portion of a device for inserting an intervertebral device according to an embodiment of the present invention;

FIG. 26 is an isometric view of a portion of a device for inserting an intervertebral device according to an embodiment of the present invention;

FIG. 27 is an isometric view of a portion of a device for inserting an intervertebral device according to an embodiment of the present invention;

FIG. 29 is an isometric view of a portion of a device for inserting an intervertebral device according to an embodiment of the present invention;

FIG. 30 is an isometric view of a portion of a device for inserting an intervertebral device according to an embodiment of the present invention;

FIG. 31 is an isometric view of a portion of a device for inserting an intervertebral device according to an embodiment of the present invention;

FIG. 32 is an isometric view of a portion of a device for inserting an intervertebral device according to an embodiment of the present invention;

FIG. 33 is an isometric view of a portion of a device for inserting an intervertebral device according to an embodiment of the present invention.

FIG. 34 is an isometric view of a portion of a device for inserting an intervertebral device according to an embodiment of the present invention.

FIG. 35A is an isometric view of a portion of a device for inserting an intervertebral device according to an embodiment of the present invention.

FIG. 35B is an isometric view of a portion of a device for inserting an intervertebral device according to an embodiment of the present invention.

FIG. 36 is an isometric view of a portion of a device for inserting an intervertebral device according to an embodiment of the present invention.

FIG. 37 is an isometric view of a portion of a device for inserting an intervertebral device according to an embodiment of the present invention.

FIG. 38 is an isometric view of a portion of a device for inserting an intervertebral device according to an embodiment of the present invention.

FIG. 39 is an isometric view of a portion of a device for inserting an intervertebral device according to an embodiment of the present invention.

FIG. 40 is an isometric view of a portion of a device for inserting an intervertebral device according to an embodiment of the present invention.

Figure 1:
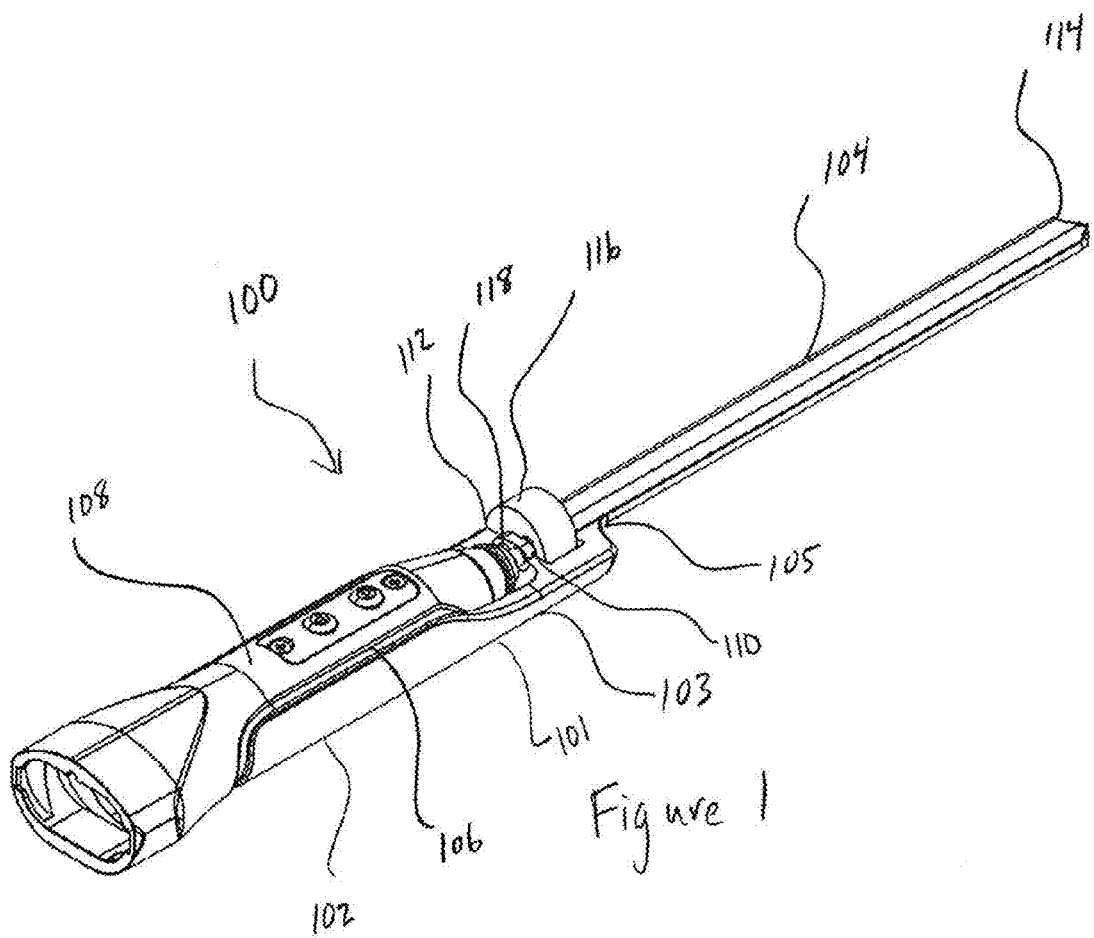
FIG. 1 is a perspective view of an introducer for inserting and distracting a distractible intervertebral body fusion device according to an embodiment of the present invention.
Figure 2:
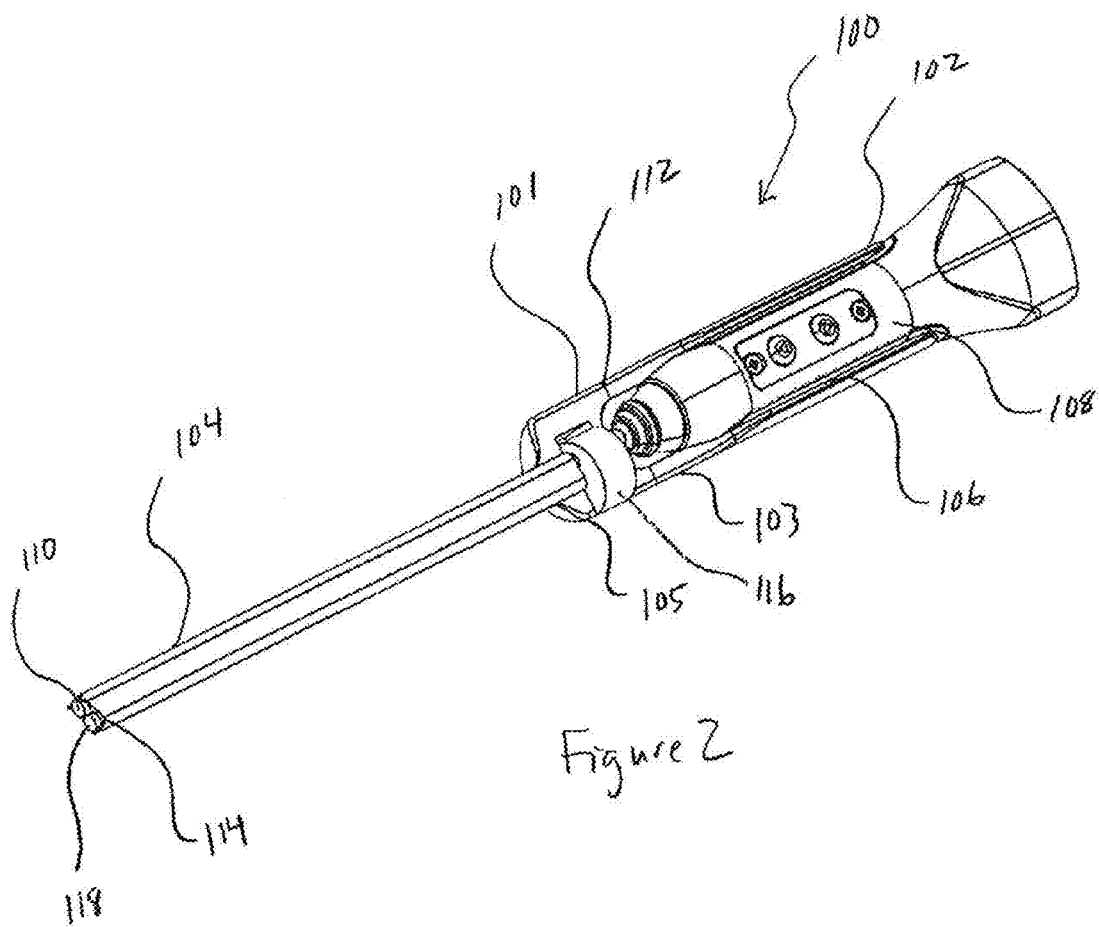
FIG. 2 is a perspective view of the introducer of FIG. 1.
Figure 3:
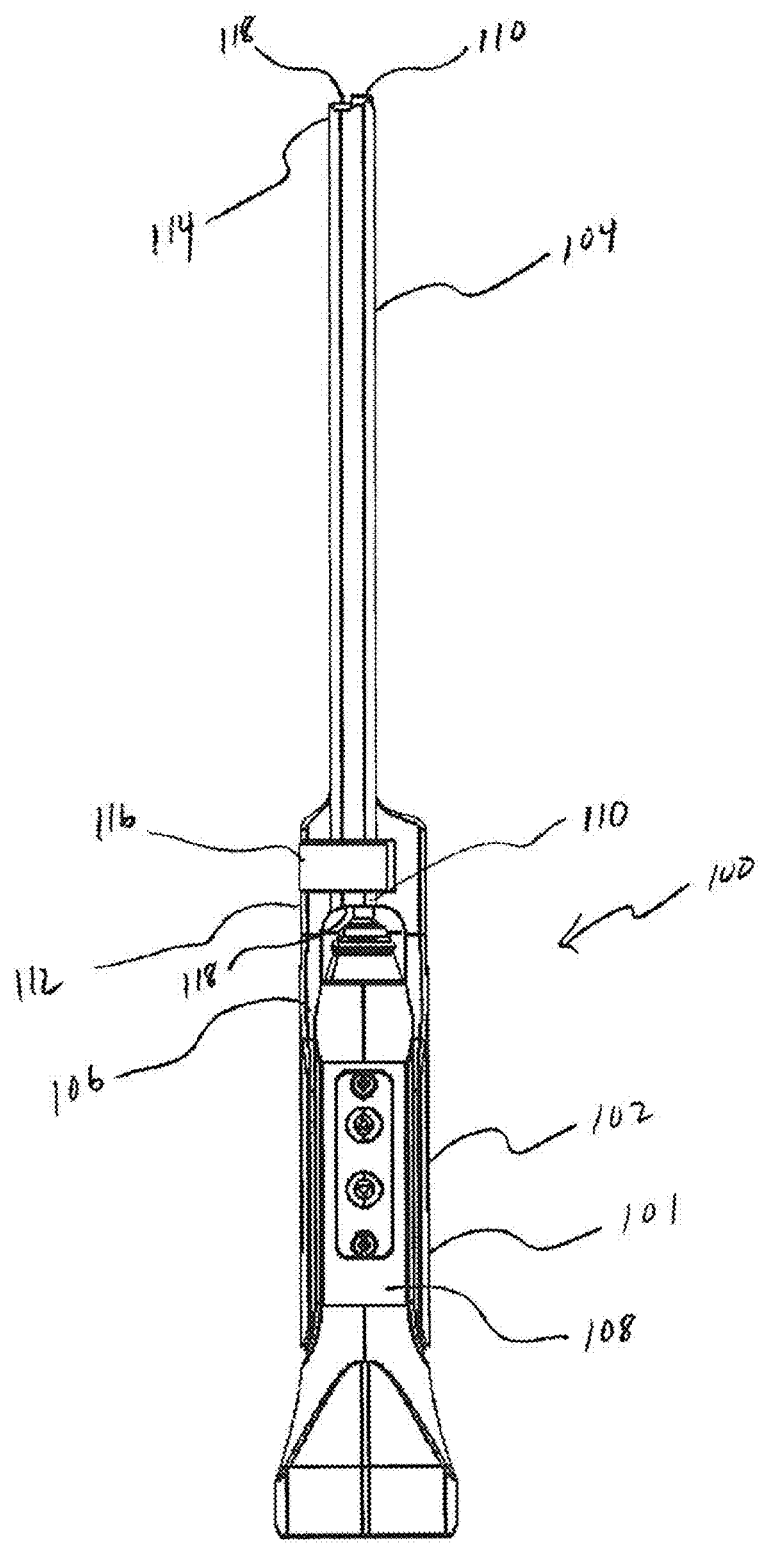
FIG. 3 is a top elevational view of the introducer of FIG. 1.
Figure 4:
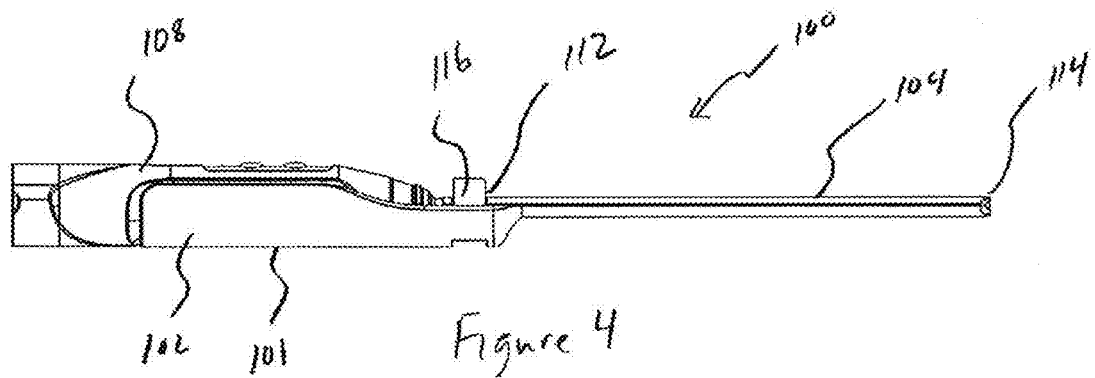
FIG. 4 is a side elevational view of the introducer of FIG. 1.
Figure 5:
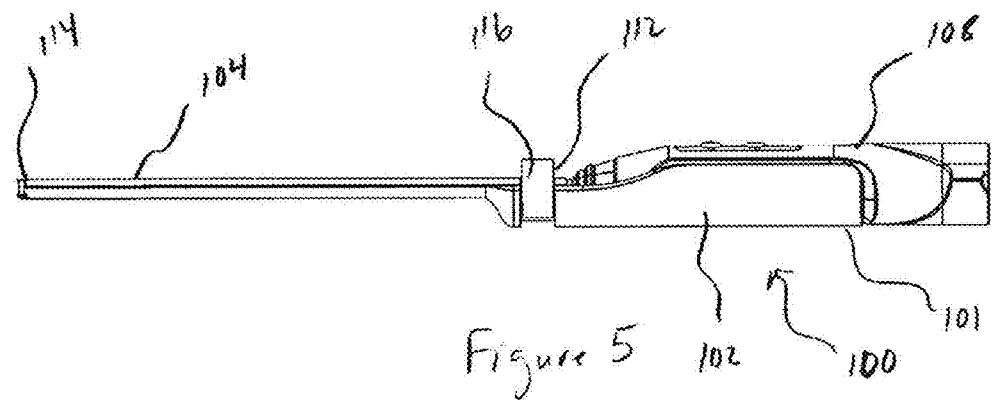
FIG. 5 is a side elevational view of the introducer of FIG. 1.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

An introducer 100 for implanting a distractible intervertebral body fusion device according to an embodiment of the present invention is depicted in FIGS. 1-5. Introducer 100 includes a body 101 including a handle 102 and a sleeve 104. In one embodiment, handle 102 can comprise a first piece 103 of an assembly and sleeve 104 can comprise the second piece of the assembly. Handle includes a slot 106 for container an actuation tool 108. In one embodiment, actuation tool 108 is a power screwdriver such as an electric screwdriver.

A drive shaft 110 can extend through sleeve 104 between a proximal end 112 of the sleeve 104 adjacent slot 106 and a distal end 114 of the device. In one embodiment, sleeve 104 can completely enclose drive shaft 110. At proximal end 112 of sleeve 104, actuation tool 108 can connect to drive shaft 110 where drive shaft 110 extends through an opening in body 101. Drive shaft 110 can extend out of an opening at distal end 114 and include a hex to engage a worm gear, drive shaft, or other actuation member of distractible device. In one embodiment, distal end 114 can be shaped to match a geometry of a portion of distractible device that it abuts. Introducer 100 can also include an adjustment knob 116. A securing shaft 118 can extend from adjustment knob 116 through sleeve 104 and out distal end 114 to interface with a tapped opening in the device. Knob 116 can be rotated to engage securing shaft 118 within the tapped opening, to stabilize device during distraction. Drive shaft 110 can extend through a slot in knob 116 such that it can rotate independently of knob 116. In one embodiment, drive shaft 110 and securing shaft 118 can be disposed at opposing outer edges of a face of the distractible device to allow for stable rotation of the device as it is being inserted.

To implant a distractible device 10 with introducer 100, the drive shaft 110 of the introducer is attached to an actuation mechanism of the distractible device and the securing shaft 118 is secured to a tapped opening of the device by rotating knob 116 and the device is inserted between adjacent vertebrae of a patient. The actuation tool 108 can be inserted into the slot 106 of the introducer 100 and connected to the drive shaft 110 at a proximal end of the sleeve 104 either before or after the device 10 is inserted into the disc space. Activation of the actuation member 108 causes drive shaft 110 to rotate, which distracts the device 10. Actuation member 108 can also be rotated the opposite direction to collapse device 10. Adjustment knob 116 provides for fine adjustment of distraction. Manual rotation of adjustment knob 116 rotates drive shaft 110 a discrete amount so that optimal distraction can be obtained. Once the device is at the desired distracted height, drive shaft 110 and securing shaft 118 can be disconnected from the device and the introducer can be removed.

Figure 18:
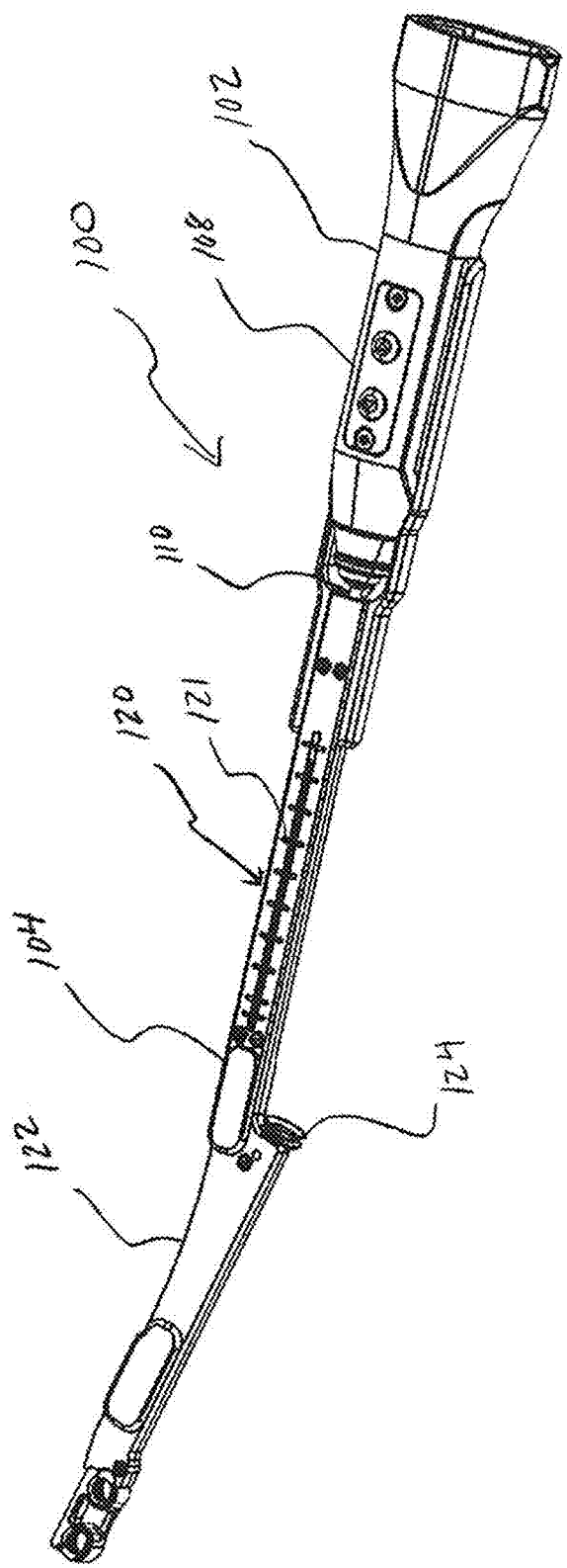
FIG. 18 is a perspective view of an introducer for inserting and distracting a distractible intervertebral body fusion device according to an embodiment of the present invention.
Figure 24:
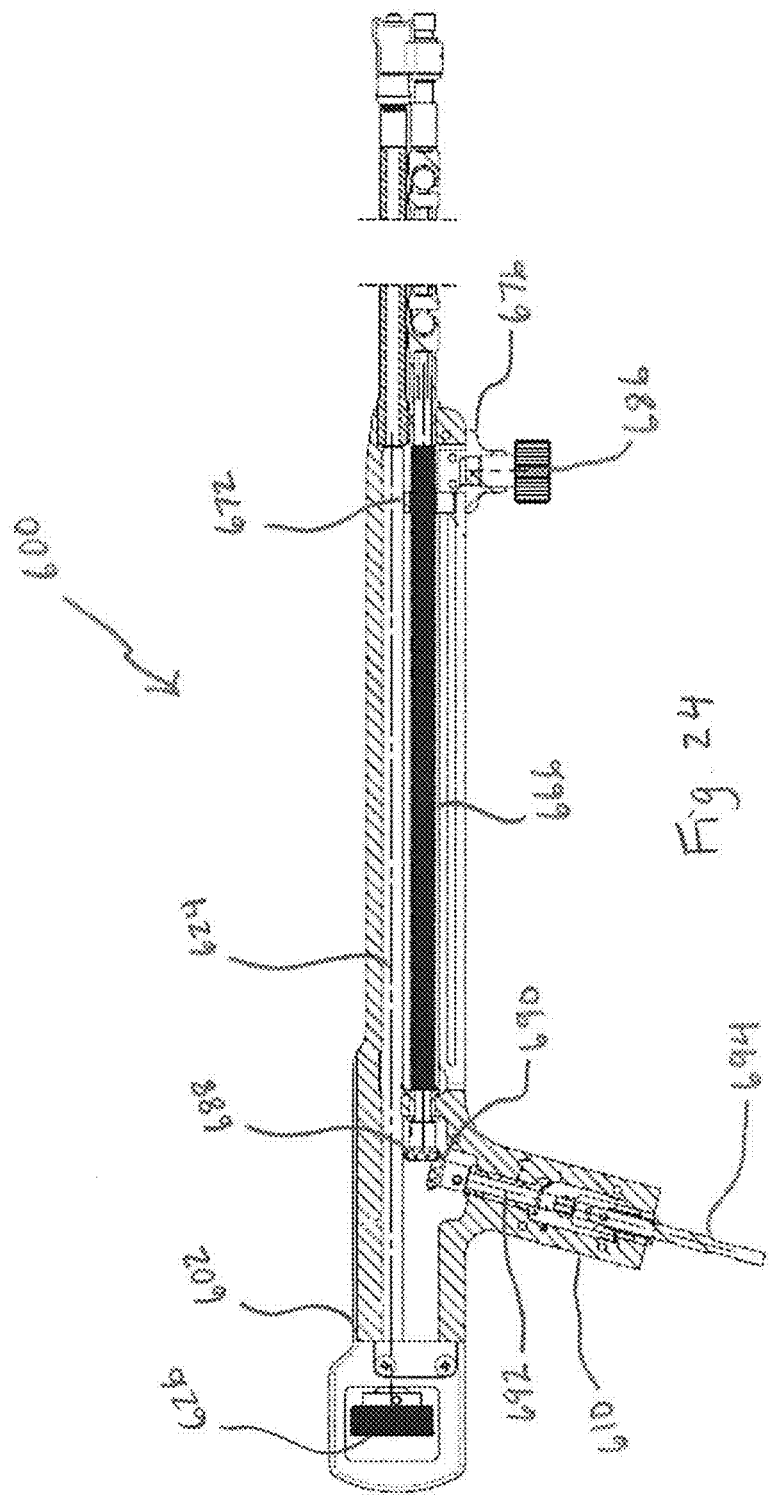
FIG. 24 is a cross-sectional view of a portion of the device of FIG. 19.

FIG. 18 depicts a variation of introducer 100 that includes additional features. Introducer 100 includes a graduated section 120 having markings 121 to indicate that amount by which the distractible device has been distracted. As the drive shaft 110 is turned with the actuator a slider or wheel can travel along graduated section to indicate the height of distraction as correlated to the amount that the drive shaft 110 has rotated. Introducer also includes offset portion 122 of sleeve 104. Offset portion 122 allows for easier insertion into the disc space and also allows for an impact surface 124. Impact surface 124 provides an area at which a hammer or other similar device can be used to tap the offset shaft 122 when the distractible device is initially inserted, which provides for easier insertion of the device.

Figure 6A:
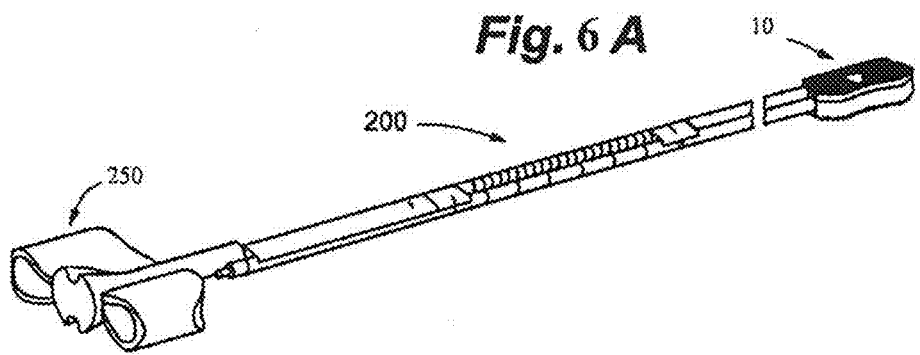
FIG. 6A is a perspective view of an introducer for inserting and distracting a distractible intervertebral body fusion device according to an embodiment of the present invention.
Figure 6B:
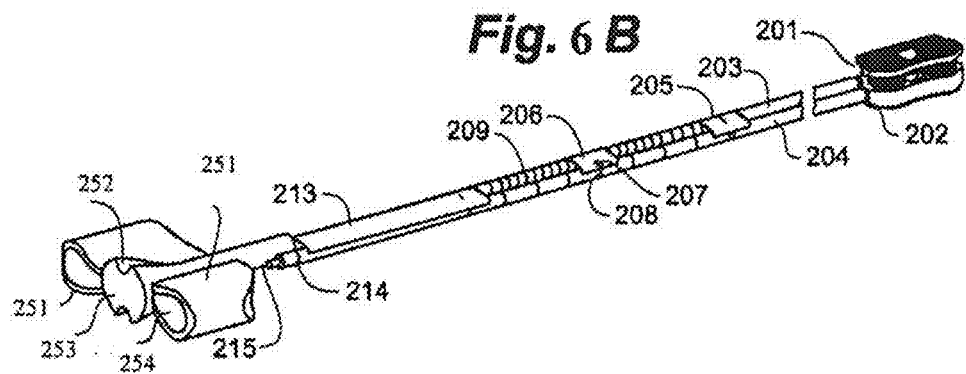
FIG. 6B is a perspective view of the introducer of FIG. 6A.
Figure 6C:
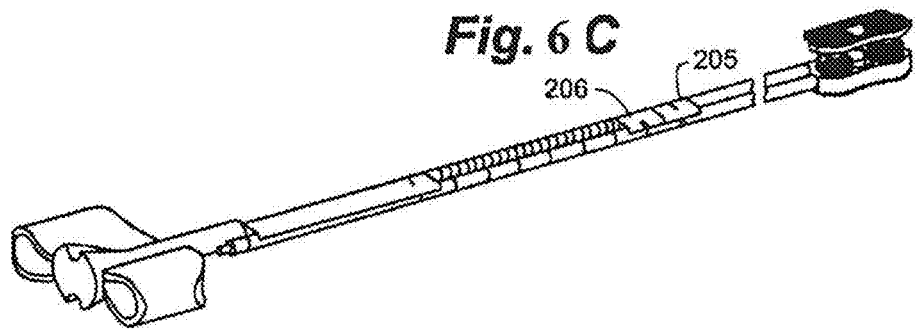
FIG. 6C is a perspective view of the introducer of FIG. 6A.

Another introducer for implanting a distractible intervertebral body fusion device 10 according to an embodiment of the present invention includes a delivery system 200 and an actuation tool 250 and is depicted in FIGS. 6A-6C. Intervertebral body fusion device 10 is depicted in FIG. 6A in a compressed configuration, in FIG. 6B in a partially distracted configuration, and in FIG. 6C in a fully distracted position. Delivery system 200 includes actuation tool 250 for actuating the distraction.

To distract the device 10, a hex of device 10 is first connected to the delivery system 200 via a socket driver on an end 201 of delivery shaft 203. In order to more securely attach the device 10 and the delivery system 200, a threaded end 202 of delivery shaft 204 can be threaded into a tapped hole in device 10 adjacent the hex. The device 10 can then be inserted into the body via a standard transforaminal lumbar interbody fusion (TLIF) or posterior lumbar interbody fusion (PLIF) procedure using the delivery system 200. A lateral interbody fusion through the lateral retroperitoneal corridor is another approach. The delivery system 200 can guide the location of the device 10 as it is being inserted with use of handle 213.

Delivery system 200 includes a hex 215 and a circumferential groove 214 at the near end of delivery shaft 204, and also has a hex and circumferential groove (not pictured) at the end of delivery shaft 203. Once the device 10 is in the disc space, the actuation tool 250 can be connected to the delivery system by engaging an internal hex socket driver of the actuation tool with the hex on the end of the delivery shaft 203, 204. In some embodiments, an internal snap ring or circumferential spring in actuation tool 250 can engage the circumferential groove on delivery shaft 203 to ensure that the actuation tool 250 does not become accidentally disengaged during use.

Figure 6D:
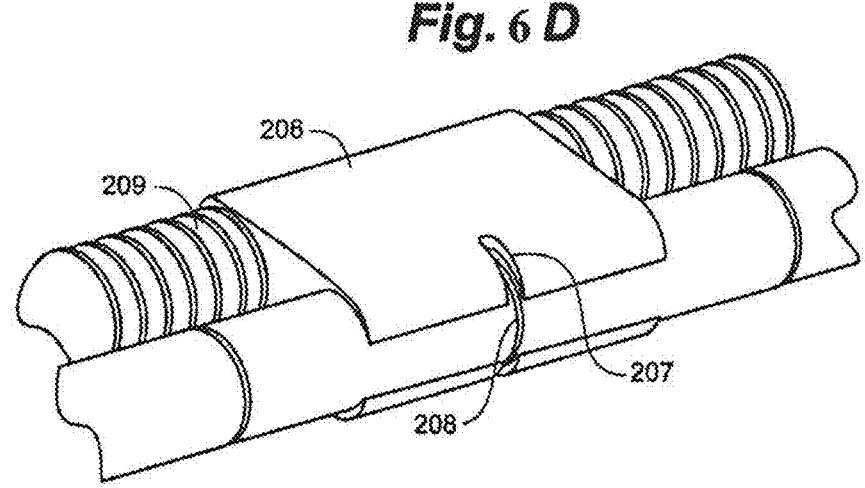
FIG. 6D is a partial perspective view of the introducer of FIG. 6A.

By turning the actuation tool 250, the user transmits torque down the delivery shaft 203 to a worm drive in device 10, which distracts the device 10. As the delivery shaft 203 is turned, a slider 206 advances along threads 209 on shaft 203. The height of the device 10 as it is expanded can be represented on the delivery system 200 by the position of the slider 206 along the delivery shaft 204 with fiducial marks 208, as shown best in FIG. 6D. Marks 208 may be positioned at any desirable interval along delivery shaft 204, and the slider 206 may include a viewing slot 207 for more complete viewing of the marks 208 as they are reached by slider 206. In one embodiment, each mark 208 can represent a distracted height of 1 millimeter.

Delivery system 200 can be configured so that when the device 10 reaches its maximum desired height, slider 206 abuts stop 205 so that it can be advanced no further, thus limiting the height of the device 10. By allowing the delivery system 200 to limit the expansion, any damage due to excessive torque is immediately apparent in the delivery system 200, so no damage is sustained by the device 10. In another embodiment, the device 10 can limit its own expansion by welding two gear teeth 424, on a threaded geared sleeve that distracts the device together so that they bind with the worm when the device 10 has reached its maximum desired height. Similarly, in other embodiments, one or more of the gear teeth can be omitted or a small post can be inserted into the interstitial space between two gear teeth to limit the expansion of the device.

In one embodiment, a lever for applying torque to the shaft 204 may be affixed to the hex 215 at the end of shaft 204. The lever may be shaped and oriented such that when the device 10 is appropriately engaged with the delivery system 200, the position of the lever allows access to the shaft 203, whereas when the device is not appropriately engaged, the lever does not allow access to the shaft 203. In another embodiment, the slider 206 may be contained with the handle 213 in order to reduce the length of the delivery system 200. In another embodiment, a tube able to carry loading in torsion may be implemented around one of the shafts 203, 204 to add to the structural rigidity of the delivery system. A small foot may be affixed to the tube to additionally support the ability of the delivery system to carry, and transmit, loading in torsion by and to the device. In another embodiment, the shaft of the delivery system 200 can be curved or bayonet in shape to allow visualization through a minimally invasive system and working channel.

The actuation tool 250 can include a recess or loop 254 that allows that user to spin the actuation tool 250 with a single finger and/or large gripping surfaces 251 that the user can grasp to turn the actuation tool 250. In one embodiment, the loop may be lined with a slippery or bearing surface to enable the loop to spin easily around the user's gloved finger(s). The actuation tool 250 can also include a broad surface 253 designed to receive the impact of a hammer for implantation. Recesses 252 can also be included on actuation tool 250 to afford the user an improved view of the device 10 while it is being implanted. Actuation tool 250 can span both delivery shafts 203, 204 and may extend over and/or receive handle 213 of delivery system 200. In another embodiment, rather than being driven by manual actuation tool 250, the device 10 can be driven by a powered actuation implement such as a pneumatic or electric drill or a motorized screwdriver mechanism, which, in some embodiments, can allow the tool to be controlled remotely.

In some embodiments, the actuation tool, manual or automatic, employs sensors in the device to transmit data regarding the implantation parameters and environment, such as device load and muscular tension, to an operator or operating system to improve the performance of the surgical procedure and outcome. The delivery system could use small strain gauges located on the device and/or load cells attached to the delivery shafts and actuation tool to measure loads present during the implantation and distraction process. These gauges and/or load cells could be monitored by a microcontroller board located on the delivery system and the information fed back to a monitoring computer via a standard interface such as a USB or wireless connection. This information could be used to closely monitor a procedure's progress, warn of impending problems and improve future procedures. If not fully bridged, the gauges could be configured as half bridges within the device and completed outside of the device. Standard signal conditioning amplifiers could be used to excite and condition the signal to yield a measurable output of voltage and current.

Figure 8:
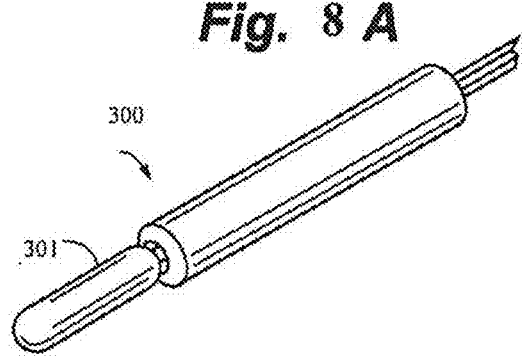
FIG. 8A is a partial perspective view of an embodiment of an introducer according to an aspect of the present invention.
FIG. 8B is a partial top view of the introducer of FIG. 8A and a distractible intervertebral body fusion device according to an aspect of the present invention.
FIG. 8C is a partial perspective view of the introducer of FIG. 8A.
Figure 8:
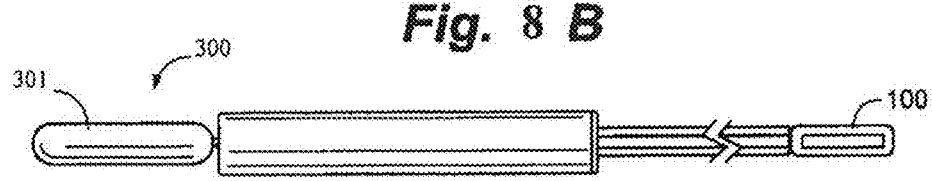
Figure 8:
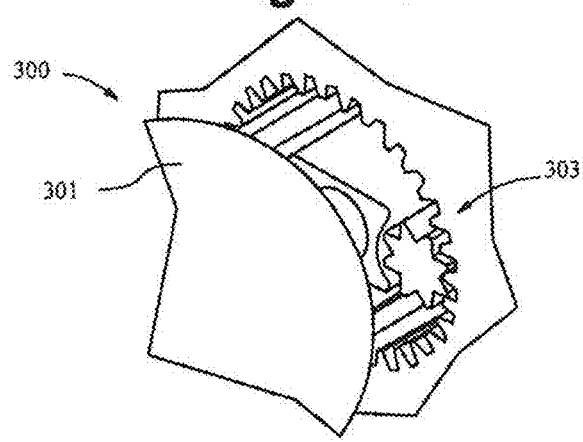

An introducer or insertion tool 300 according to another embodiment of the present invention that can be used to place a device 12 between adjacent vertebra or vertebral bodies and used to distract the endplates of the adjacent vertebral bodies is depicted in FIG. 7. Insertion tool 300 can initially be used to insert a device between vertebral bodies. In one embodiment, insertion tool 300 can include a pair of parallel screwdrivers or wrenches 302 temporarily affixed to drive screws that distract the device with retainers 304. In one embodiment shown in FIG. 7, insertion tool 300 extends rearwardly from device 12. In another embodiment, insertion tool 300 may also extend distally from device 12. In such an embodiment, device 12 can include an open nose portion and rear portion to allow it to be threaded onto insertion tool 300 and insertion tool 300 can also be used to initially distract the vertebral bodies. Optionally, the insertion tool 300 can include a single handle 301 and a gear system 303 where the handle 301 has an internal gear that, when turned, turns external gears on the shafts that turn the screws on the device 12 as depicted in FIGS. 8A-C. Although separate delivery devices 100, 200, 300 have been described, it should be noted that each feature of each device could be added to any of the other devices.

Referring now to FIGS. 19-40, there can be seen an inserter 600 for inserting and expanding an intervertebral body fusion device in a patient according to another embodiment of the present invention. Inserter 600 generally includes a shaft frame 602, a drive housing 604, a support shaft 606 and a drive shaft 608. As can be seen most clearly in FIGS. 25 and 26, in one embodiment, shaft frame 602 and drive housing 604 can be connected by inserting a handle portion 610 of shaft frame 602 into an opening in a distal end 612 of drive housing 604. Shaft frame 602 and drive housing 604 can then be secured together by inserting fasteners through aligned apertures 614, 616 in handle portion 610 and distal end 612. Support shaft 606 and drive shaft 608 extend from a distal end 618 of shaft frame 602 for connecting to a device 10 for insertion into a patient.

It can take significant force to insert an implantable device into a disc space. Often it is necessary to strike the inserter with an object such as a mallet to force the implant into the disc space. Shaft frame 602 can therefore include a proximal end 603 strong enough to accommodate striking by a mallet or other object and that does not contain any components that may be damaged by absorbing such force. The drive housing 604 can extend outwardly from the shaft frame 602 at a point along the frame displaced from the proximal end 603 to avoid damage to the drive mechanism in drive housing 604. Such a configuration also allows for greater visualization of the procedure when working through a minimally invasive working channel tube (for example, 18-24 mm diameter) because the drive housing does not interfere with the view. In some embodiments, the drive housing, which along with the drive mechanism can function as a handle for the inserter 600, can be oriented at an angle greater than or less than ninety degrees from the shaft frame 602 for a more ergonomic handle that allows the device to be inserted at an appropriate angle.

One embodiment of a support shaft 606 for use with inserter 600 can include a rod 624 as shown in FIG. 30 and a sleeve 621 as shown in FIG. 29. Rod 624 can include a wider proximal portion 623, a narrower distal portion 625, and a connecting end 627. Sleeve 621 can include a threaded distal end 620 and a connector 622 at proximal end. Distal portion 625 of rod 624 can be received within sleeve 621, with connector 622 of sleeve 621 mating with proximal portion 623 of rod 624. Proximal portion 623 extends through shaft frame 602 and connects at a proximal end with a clamp knob 626. In one embodiment, proximal portion 623 of rod 624 is connected to clamp knob 626 with a pin that extends through clamp knob 626 and into rod 624. Thus, rotation of knob 626 causes rotation of support shaft 606.

In one embodiment, drive shaft 608 can include a sleeve 630 (FIG. 31), a drive link 632 (FIG. 32), a pair of joints 634 (FIG. 27) and a driver 636 (FIG. 33). As can be seen in FIGS. 19-21 and 34, a first joint 634A can extend distally from shaft frame 602. Each joint 634 can have connector ends 638, 640 connected by a pivot joint 642. Second connector end 640 of joint 634A can extend into sleeve 630. Drive link 632 can extend through sleeve 630 and between first joint 634A and a second joint 634B. As shown in FIG. 34, which is shown without sleeve 630 for the sake of clarity, a recessed portion 644 of drive link 632 can have a spring 646 disposed thereon. In addition, first joint 634A can include a slot 641 to which drive link 632 is attached with a pin 633 to allow longitudinal movement of drive link 632 that is biased by a biasing member, such as spring 646. In one embodiment, second joint 634B does not include such a slot, and is connected to the distal end of drive link 632 with a pin 633 that extends through a conforming aperture. First connector end 638 of second joint 634B can connect to driver 636. This configuration of drive shaft 608 allows a single drive shaft configuration to have the rotational and longitudinal flexibility to be used to expand implantable devices of various sizes and configurations.

Figure 28C:
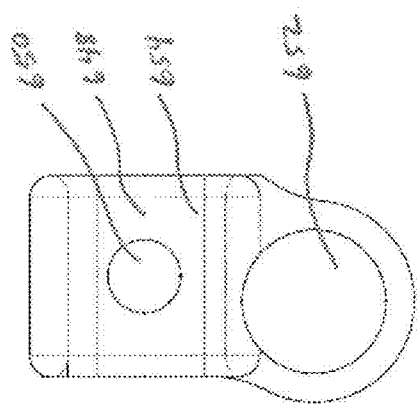
FIG. 28C is a front end view of the portion of FIG. 28A.
Figure 28B:
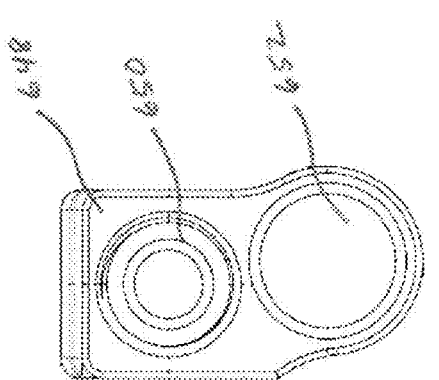
FIG. 28B is a rear end view of the portion of FIG. 28A.
Figure 28A:
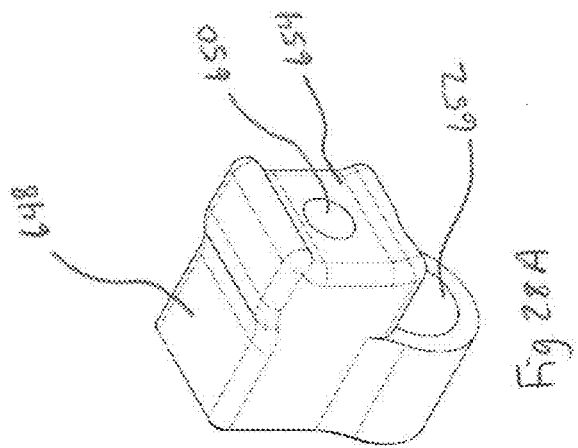
FIG. 28A is an isometric view of a portion of a device for inserting an intervertebral device according to an embodiment of the present invention.

A device interface 648, shown in detail in FIGS. 28A-28C, can be positioned at a distal end of shafts 606, 608. Device interface 648 can include an upper, support shaft aperture 650 and a lower, drive shaft aperture 652. An upper distal surface 654 of interface 648 can conform to a shape of a device 10 to be inserted as shown in FIGS. 35A-B. In one embodiment, a plurality of differently configured device interfaces can be provided with inserter 600 such that a particular device interface that conforms to a particular device to be inserted into a patient can be selected for a procedure. Threaded distal end 620 of sleeve 621 can screw into a first threaded portion of upper aperture 650. Connecting end 627 of rod 624 can then extend through sleeve 621 and first portion of upper aperture 650 and through a second, narrower portion of upper aperture 650, as shown in FIG. 35B, to attach and connect directly to device 10. A gem nut 656 can be threaded onto the threaded distal end 620 and used to tighten the connection between the device interface 648 and shaft 606 with device 10. Driver 636 can extend through the lower aperture 652 through device interface 648 to connect drive shaft 608 to the device 10. Driver 636 can be connected to a drive mechanism of the device 10, such that rotation of driver 636 causes expansion of device 10. A bushing 658 can extend through aperture 652 to aid in securing the connection. In one embodiment, device interface 648 is customized to be shaped to interface with a particular implantable device 10 and can be interchangeable with other device interfaces for use with implantable devices of other configurations. Driver 636 and bushing 658 can also be customized for use with a particular implantable device 10. In one embodiment, driver 636 and bushing 658 are formed as unitary components of device interface 648.

Shaft frame 602 of inserter 600 can also include a height indicating mechanism that indicates and can restrict a height of the expanded device as it is expanded with the drive shaft 608. A cover plate 660 (FIG. 37) having height markings 662 and an elongate slot 664 can be positioned on one or both sides of shaft frame 602. Within frame 602 as shown, for example, in FIG. 36, a threaded shaft 666 (FIG. 38) can extend behind the cover plate 660. Threaded shaft 666 can included a threaded body 668 between a proximal end and a distal end. Distal end can include a connector 670 that extends through the shaft frame 602 for connection with the first joint 634A of drive shaft 608. Threaded shaft 666 can therefore also be considered a part of the drive shaft 608 assembly. An indicator nut 672 (FIG. 39) can be threadably received along threaded shaft 666, such that rotation of threaded shaft 666 causes the indicator nut 672 to advance along the shaft 666. A projection 674 can extend outwardly from indicator nut 672 through slot 664 in cover plate 660 to indicate the height of the distracted device 10.

Inserter 600 can also include a block stop 676 for limiting the amount by which the inserter 600 is capable of expanding the implantable device. Block stop 676 (FIG. 40) can include a stop 678 and a pair of projections 680. Block stop 676 can be slidably attached to frame 602 by inserting fasteners through a frame slot 682 through frame 602 and apertures 684 through stop 678. Projections 680 can extend outwardly of slots 664 in cover plates 660 to provide an indication of a desired and/or maximum implant distraction height. A knob 686 can be used to tighten block stop 676 to fix it in the desired position. As the drive shaft 608 is rotated to expand the implantable device the indicator nut 672 translates along the threaded shaft 666. When the indicator nut 672 reaches the block stop 676, the stop 678 provides a mechanical stop that blocks the indicator nut 672 from moving further forwards, effectively locking the drive shaft 608 from being further rotated to expand the implantable device 10 beyond the maximum setting.

A proximal end of threaded shaft 666 can be attached to a shaft gear 688, such as, for example, a bevel gear. Shaft gear 688 can interface with a corresponding drive gear 690 as shown in FIG. 36. Drive gear 690 is connected via a linkage 692 to a drive mechanism 694 or actuation tool. In one embodiment, drive mechanism 694 can be retained in drive housing 604 with a locking tab 697. Locking tab 697 can comprise two halves with a slit therebetween. To retain an actuation tool 694 such as a screwdriver, the tool is inserted into housing and then a locking screw can be inserted into an aperture 699 extending through locking tab 697 to forcibly retain the tool in the housing 604. In another embodiment, drive mechanism 694 can be retained within device 600 by drive housing 604 and latch 696 as shown in FIG. 19A. Controls 698 can be used to operate drive mechanism 694. Activation of drive mechanism 694 causes rotation of drive gear 690, which interfaces with the corresponding shaft gear 688 to translate the rotation to drive shaft 608. As such, activation of drive mechanism 694 causes expansion of an implantable device connected at the distal ends of drive shaft 608 and support shaft 606.

Drive mechanism 694 can be, for example, an electric screwdriver. In other embodiments drive mechanism 694 can be any tool that can provide for rotation of drive gear 690 and can be powered manually or by other sources, such as air power. In some embodiments, the handle of the device can incorporate a clutch mechanism allowing the drive mechanism to be selectively engaged with the drive shaft. Clutch mechanism allows the RPM's and torque of the drive mechanism to be varied because drive portion of drive mechanism can be connected to drive shaft via clutch such that they spin at the same speed or at different speeds or can be disengaged such that activation of drive mechanism does not cause drive shaft to rotate at all. This provides for easy substitution of different types of drive mechanisms, such as battery, electric, gas, air or manually powered mechanisms, such as screwdrivers, for rotating drive shaft. Control of the torque delivered by drive mechanism also reduces the risk of implant breakage and damage to the vertebral end plates of the patient.

In operation, an implantable device of a desired size and configuration is selected. A conforming device interface 648 can then be attached to a distal end of support shaft 606 and drive shaft 608. The implantable device is connected to the inserter by tightening connecting end 627 of rod 624 into an aperture in device with knob 626. The driver 636 of drive shaft 608 can be connected to a drive mechanism of the implantable device. A desired maximum allowable height for the implantable device can be set by sliding block stop 676 within slot 682 on shaft frame 602 to a desired height indicated on cover panel 660. A drive mechanism 694 such as an electric screwdriver can be actuated to rotate drive shaft 608 to expand the implantable device. The height of the implantable device as it is expanded is indicated by the indicator nut 672 advancing along the slot 664 in the cover plate 660. When the implantable device has reached its maximum allowed height, the block stop 676 will prevent the drive shaft 608 from rotating to further expand the device.

Figure 9A:
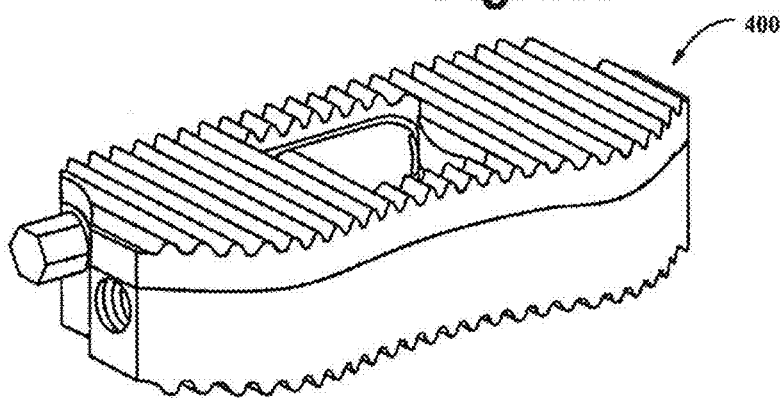
FIG. 9A is perspective view of a distractible intervertebral body fusion device according to an embodiment of the present invention in a collapsed configuration.
Figure 9B:
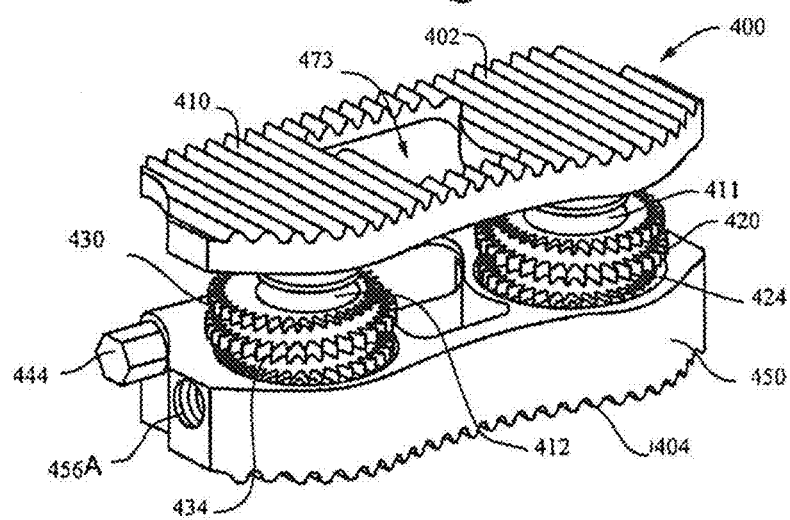
FIG. 9B is a perspective view of the distractible intervertebral body fusion device of FIG. 9A in an expanded configuration.

Referring to FIGS. 9A-9C, there can be seen a distractible intervertebral body fusion device 400 adapted for implantation into an intervertebral disc space of a patient according to an embodiment of the present invention. FIG. 9A shows the device 400 in a fully compressed configuration, FIG. 9B shows the device 400 in a fully expanded configuration, and FIG. 9C shows an exploded view of the device 400. Introducers as described herein can be used to insert the device 400 between adjacent vertebrae of a patient and distract the device to expand the disc space.

Device 400 includes a first member 410 having a bearing surface 402 configured to interface with an end plate of one of a superior or an inferior vertebra of the intervertebral disc space and a second member 450 having a bearing surface 404 configured to interface with an end plate of the other of the superior or inferior vertebra. In one embodiment, the bearing surfaces 402, 404 can include a textured surface, such as that provided by corrugations 414, to create friction with the end plates of the vertebra to prevent accidental extrusion of the device 400. The radii of the corrugation 414 valley and the corrugation 414 top width can be maximized to minimize the notch factor and reduce stress while still providing a corrugation design that reduces the propensity of the device 400 to extrude from the disc space. One or both of the members 410, 450, can also include an opening 473, 453 extending through the member for facilitating bone growth through the device 400. In other embodiments, opening can be filled with a gel, rubber, or other complaint material that can replicate the nucleus of an intervertebral disc and supplement the strength of the device in compressive, shear, and torsional loading conditions. Alternatively, a generally solid surface, a textured or etched surface, a scored or notched surface, or a surface with multiple openings can be provided on each member 410, 450.

Device 400 can also include a pair of coaxial screw gear sleeve mechanisms including threaded post members 411, 412 extending from first member 410 and a pair of threaded geared sleeves 420, 430 configured to surround the post members 411, 412. Threaded post members 411, 412 can have threads 413, 415 defined on an exterior surface thereof. Threaded geared sleeves 420, 430 can have both interior threads 422, 432 configured to interface with the threads 413, 415 of threaded post members 411, 412 and exterior threads 421, 431. In one embodiment, both the exterior 421 and interior 422 threads of one of the sleeves 420 are of an opposite hand to the threads 431, 432 of the other sleeve 430. External threads 421, 431 of sleeves 420, 430 can have gear teeth 424, 434 cut into the thread. In one embodiment, the gear teeth 424, 434 are not cut down to the root, or minor diameter, of the threads 421, 431 in order to maximize the strength of the threads. In the compressed configuration, threaded geared sleeves 420, 430 can fit within sleeve openings of 461, 462 in second member 450. Openings 461, 462 can include threaded portions 451, 452 that mesh with exterior threads 421, 431 of threaded geared sleeves 420, 430. In one embodiment, sleeve openings 461, 462 extend all the way through bearing surface 404 of second member 450. In some embodiments, as pictured, threaded geared sleeves 420, 430 can be substantially solid. In other embodiments, threaded geared sleeves can include one or more slots through the sleeve for mass reduction and material savings or to promote bone in-growth.

The device 400 can be expanded with the aid of a worm 440 that extends through a worm aperture 454 in the device 400 and can be driven with an introducer as described herein. The worm 440 can have first 442 and second 441 opposing threaded sections configured to interface with the exterior threads having gear teeth 424, 434 of threaded geared sleeves 420, 430 through a pair of apertures 457, 458 in threaded portions 451, 452 of sleeve openings 461, 462. The worm 440 can include a hex 443, 444 at each end of the worm 440 that allows it to be driven by an introducer/delivery system. Such a delivery system can also be attached to the device 400 when driving the worm 440 at tapped hole 456A or tapped hole 456B to stabilize the delivery system. Device 400 can include a hex 443, 444 and tapped hole 456A, 456B at each end of device, so that the device 400 can be inserted and driven from either end, or can include a hex and tapped hole at only one side of the device, limiting the device to insertion and distraction from a single direction. Bottom member 450 can also include one or more scallops 455 above the worm aperture 454 that provide increased strength and thickness while still allowing the threaded geared sleeves 420, 430 to rotate. Further detail regarding distractible intervertebral body fusion device such as device 400 can be found in U.S. Patent Application Publication No. 2011/0160861, which is hereby incorporated by reference herein.

A partial sectional view of a distractible intervertebral body fusion device 400 in FIG. 9D, helps illustrate how the device can employ multiple coaxial screw gear sleeve mechanisms as telescoping mechanisms utilizing the threaded post members 411, 412, threaded geared sleeves 420, 430 and the worm 440 to expand the first member 410 and second member 450 relative to each other. By turning hex 444 counterclockwise, and therefore the worm 440 counterclockwise, first threaded section 442 of worm 440 pulls the gear teeth 434 of threaded geared sleeve 430 towards the hex head 444. This causes the sleeve 430 to translate upward from the second member 450 along internal threads 452. As the sleeve 430 rotates while it translates upward, the threaded post member 412 extending from the first member 410, which is unable to turn, also translates upward with respect to the sleeve 430 and the second member 450. This second translation results from the opposite handed external threads 415 of the threaded post member 412 being driven by the matching internal threads 432 of the sleeve 430. The same mechanics are occurring on the other side of the device with oppositely threaded sleeve 420 having external threads 421 and internal threads 422, post member 411 having external threads 413 and second threaded section 441 of worm 440.

Because the threads for like components for each device are opposite handed, the threads 442 on one side of the worm 440 will be pulling the gear teeth 434 of the threaded geared sleeve 430 while the threads 441 on the other side of the worm 440 will be pushing the gear teeth 424 on the other sleeve 420, or vice versa depending on the direction of rotation of the worm 440. These opposing forces applied to the worm 440 by the threaded geared sleeves 420, 430 are carried in either tension or compression by the worm 440. Therefore, the worm 440 is not substantially driven into or out of the worm aperture 454 as the device 400 is expanded or contracted. This is advantageous in that a pin or other retainer is not required to retain the worm and balance the forces in the device. Such a pin can be a point of excessive wear which can cause the life cycle of the device to be shorter lived. In some embodiments, a pin can be employed to prevent the worm 440 from being able to be pulled or pushed axially, which can cause the device to become jammed.

Alternative drive mechanisms to worm drive include piezoelectric actuators and any momentum imparting collision mechanism or configuration. Additionally, a drive mechanism, such as a worm, could be an integrated part of a delivery system or introducer. In such an embodiment, the external threads of the threaded geared sleeves would both be of the same hand and the worm would be screwed into the compressed device in the worm aperture. As the worm is turned, the axial position of the worm would be constrained by the delivery system, instead of a pin, resulting in distraction of the device. Once the device reached the desired height, the worm could be screwed out of the worm aperture and the device could be locked in place by screwing in a threaded locking worm. The locking worm could have an additional threaded or snapping feature that enables it to be permanently, or in a removable fashion, attached to the device. The locking worm could be made from a radio transparent material such as PEEK, which would therefore allow imaging through the worm. The locking worm would only need to be strong enough to inhibit the threaded geared sleeves from turning into or out of the device, and would not need to be strong enough to cause the device to distract. A larger radio transparent window could be formed by removing a portion of the sides of the bottom member on either side of the opening in the bottom member along the length of the device, so long as the device retained a necessary amount of stiffness.

Referring now to FIGS. 10A and 10B, a preferred fit of gear teeth 424, 434 of threaded geared sleeves 420, 430 in internal threaded portions, 451, 452 of second member 450 is shown. As the gear teeth 424, 434 are thrust towards the internal threads 451, 452 of the second member 450 by the worm, the load between the gear teeth 424, 434 and threads 451, 452 is balanced by the bearing surfaces 463, 464 between the components, which results in the ability of the device 400 to distract a substantial load. This fit between the gear teeth 424, 434 and the internal threads 451, 452 can be contrast with the fit shown in FIGS. 11A and 11B. In those figures, when the gear teeth 424', 434' of the threaded geared sleeves 420', 430' are thrust towards the internal threads 451', 452' of the second member 450', the force is not balanced by bearing surfaces as in FIG. 2B, but by the force the internal threads 451', 452' apply to the gear teeth 424', 434'. This can result in the gear teeth 424', 434' acting as a wedge and becoming jammed against the internal threads 451', 452', which dramatically reduces the ability of the device to distract substantial loads and makes the device more sensitive to friction between components. Optionally, a liquid or gas lubricant, such as silicon lubricant, may be used to reduce friction in the mechanism. Saline may also be used as a lubricant.

It should be noted that although the threads depicted in the Figures are all screw threads in the form of projecting helical ribs, "thread" for the purposes of the present invention can also refer to any other mechanism that translates rotational force into translational or longitudinal movement. For example, in some embodiments threads can be comprised of a recirculating or spiral arrangement of bearings or any other low friction arrangement, such as cooperating magnets.

In one embodiment, the height of the device 400 between the bearing surfaces 402, 404 in the fully compressed configuration is 6.5 millimeters and the maximum fully distracted height is 12 millimeters, thus providing a very large amount of distraction relative to the initial height of the device. The maximum height is defined by the largest height at which the device can meet the dynamic compressive, shear, and torsional requirements for implantable intervertebral body fusion devices. Variables that determine this height include the width of the threaded geared sleeves, which is limited by the desired width of the device, and the material from which the device is made. With regard to the material for the device, materials with higher fatigue performance allow the maximum height of the device to be taller even with a narrower width. In one embodiment, the device is made from titanium. The device may also be made from cobalt chrome, MP35N, or PEEK, for increased strength characteristics or increased radiolucent characteristics, depending on the material. X-ray transparency is a desirable property because it allows for the fusing bone to be imaged through the device. In one embodiment, the device can be designed such that in the compressed configuration the threaded geared sleeves project through the bearing surface of second member in order to provide for an even greater amount of distraction. To accommodate the device on implantation, openings configured to contain the projecting portions of the sleeves can be cut into the adjacent vertebral end plate.

Once distracted, device 400 does not require a locking mechanism to maintain the desired height within the body. This is because, when driven backwards, the device exhibits a very high gear ratio which causes even the slightest friction in the system to overwhelm any amount of compression, torsion, or shear loading that might be applied to the device. In dynamic testing in shear, torsion, and compression, the maximum amount by which the height of the device changed was by approximately 0.01 millimeter. The device 400, because height can be maintained at any point along the threaded geared sleeves, therefore also exhibits very high resolution height control, on the order of 1 micrometer.

Figure 12A:
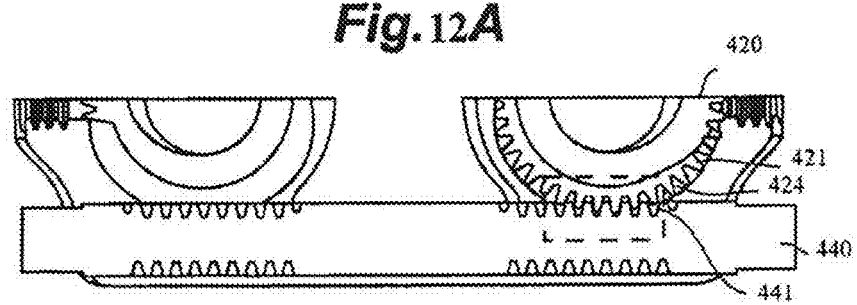
FIG. 12A is a partial top view of a distractible intervertebral body fusion device according to an embodiment of the present invention.
Figure 12B:
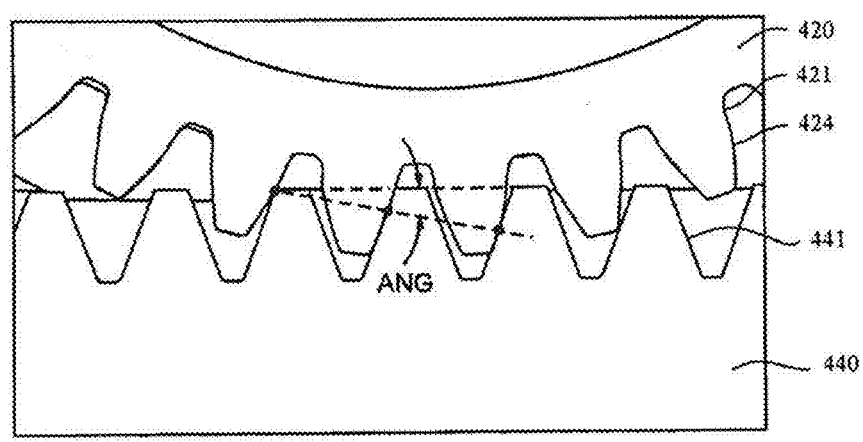
FIG. 12B is a partial top view of the distractible intervertebral body fusion device of FIG. 12A.

In one embodiment, the external threads 421, 131 and gear teeth 424, 434 on the threaded geared sleeves 420, 430 can be substantially trapezoidal in shape. In one embodiment, the thread is a trapezoidal 8 millimeter by 1.5 millimeter metric thread. A trapezoidal design enables a relatively large gear tooth size and, accordingly, a larger area over which the distraction loading is distributed. Additionally, with precise manufacturing, multiple gear teeth 424, 434 on the threaded geared sleeves 420, 430 can be engaged by the worm 440 at the same time along the pressure angle ANG, as shown in FIGS. 12A and 12B. Distributing the distraction load over multiple teeth of the sleeves 420, 430 and the worm 440 is critical to achieve the minimum device size while providing a maximum amount of distraction and load capacity.

In one embodiment, a distractible intervertebral body fusion device similar to device 400 can include a two part worm that provides for differential distraction of the device. One example of such a device is disclosed in U.S. Patent Application Publication No. 2011/0160861, the entire disclosure of which is incorporated by reference herein. The two part worm can include a first portion having a first threaded section for engaging a first threaded geared sleeve and a second portion having a second threaded section for engaging second threaded geared sleeve. In one embodiment, the two portions of the worm are connected to each other. The two portions of the worm rotate independently of each other. Thus, each threaded geared sleeve can be rotated separately to be distracted different amounts, which provides the ability to angle the top member of the device. Such a configuration can accommodate lordotic or kyphotic geometry. An inserter to distract such a device can otherwise have similar features to the inserters described herein but include a pair of drive shafts. In one embodiment, each drive shaft can be operably connected to a different actuation mechanism. Such an inserter would therefore include three elongate shafts—a single support shaft and a pair of drive shafts.

In one embodiment, distractible intervertebral body fusion devices as described herein can be made of titanium and the delivery system/introducer can be made primarily out of stainless steel. Components of each mechanism that slide against each other can be made of different types of the general material. For example, the first member can be made from Ti 6Al 4V standard titanium, which has high smooth fatigue performance, while the threaded geared sleeves can be made from Ti 6Al 4V ELI, which has high notched fatigue performance. Such a combination results in each component being made out of a preferred material for its fatigue notch factor while the overall mechanism implements different materials where components are slidably arranged.

In various embodiments, device is shaped to be ergonomic. Device can have various shapes, such as, for example, rectangular, kidney, or football shaped. A kidney or football shaped device maximizes contact between the device and the vertebral bodies because the end plates of vertebrae tend to be slightly concave. One or both ends of the device may also be tapered in order to facilitate insertion. This minimizes the amount of force needed to initially insert the device and separate the vertebral bodies. In addition, the device may be convex along both its length and its width, or bi-convex. Device can be constructed in various sizes depending on the type of vertebra and size of patient with which it is being used.

Device can be manufactured in various ways with, in some embodiments, different components of the device can be manufactured in different ways. In one embodiment, thread milling can be implemented to manufacture the various threads in device. Wire EDM can be utilized to manufacture some or all of the holes and openings in the device. Assembly jigs and post processing steps can also be utilized to allow the device to be manufactured to exacting standards.

In one embodiment, the surface of the device can be treated to minimize surface roughness or to reduce pitting of the material within the body. A rough surface or pits can increase the stress on the device, which can result in shortening of the fatigue life and/or reduce fatigue strength. In one embodiment, the surface can be treated with electro-polishing, both removing burrs from the edges of the device and finishing the surface. In another embodiment, the surface can be left untreated because a rough surface on the end plates helps prevent accidental extrusion of the device. In one embodiment, the device can also be coated with a highly elastic, impermeable material to extend its fatigue life. Specifically, the impermeable material would prevent the corrosive properties of blood from degrading the device. In another embodiment, the device can be comprised of a biocompatible material, so that no coating is necessary. In a further embodiment, the device can be made of a biodegradable material designed to degrade in the body at a selected stage of the healing process, such as after bone fusion.

Referring to FIGS. 13A-13C and 14A-14B there can be seen a distractible intervertebral body fusion device 500 according to an aspect of the present invention that can be inserted and distracted with an introducer as described herein. Device 500 includes a device body 502. Device body 502 can include a nose portion 504, a rear portion 506, a pair of opposed end plates 508, structural members 510 and flexure members 512 attaching one end of the structural members 510 to end plates 508 and the other end of structural members 510 to blocks 514a, 514b. Further details regarding distractible intervertebral body fusion devices such as device 500 can be found in U.S. Patent Application Publication No. 2010/0185291, which is hereby incorporated by reference herein.

Figure 14B:
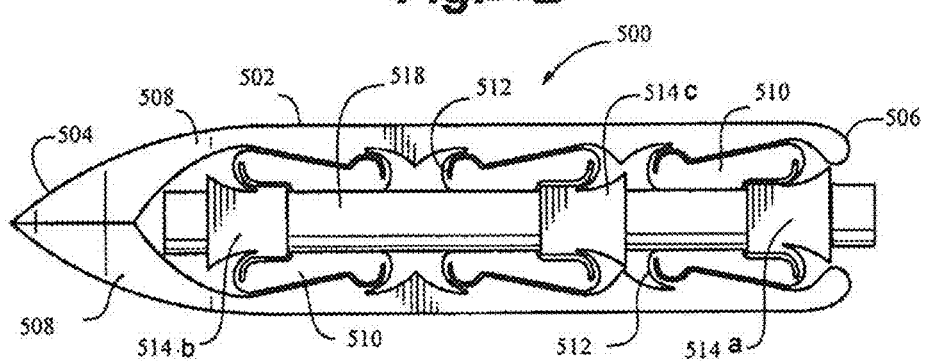
FIG. 14B is a side view of the distractible intervertebral body fusion device of FIG. 14A.

Device body 502 can include two sets of structural members 510, or struts, on each side (FIGS. 13A-13D) or can include three, or more, sets of structural members 510 on each side (FIGS. 14A-14B). As will be discussed in more detail herein, addition of a third strut provides greater stability to the device 500. Flexure members 512 are thin strips of material that connect the structural members to the end plates 508 and expansion blocks 514. The flexure members 512 allow a one-piece device 500 to behave similarly to a device having multiple parts and a rotating pin joint. Flexure members 512 can, for example, be band flexures (FIGS. 13A-13C and 14A-14B), circular flexures, elliptical flexures, or leaf flexures.

In one embodiment, each end plate 508 includes a rectangular opening 516. Opening can be used to facilitate bone growth through the device 500. In other embodiments, opening 516 can be filled with a gel, rubber, or other complaint material that can replicate the nucleus of an interverterbral disc and supplement the strength of the flexures 512 in compressive, shear, and torsional loading conditions. Alternatively, a generally solid surface or a surface with multiple openings can be provided on each end plate 508. End plates 508 can have a rough surface or teeth to create friction with the end plates of the vertebra to prevent accidental extrusion of the device 500. In one embodiment, the device body 502, or portions of the device body 502, can be overmolded with a polymer or other material to supplement the strength of the device. For example, long carbon nanotube chains can be applied to the surface of the device so that as the device distracts the carbon nanotubes align along the surface of the flexures to add to the stability of the device.

Nose portion 504 can be tapered to facilitate the insertion of the device 500 into the disc space. Rear portion 506 can also be tapered. In one embodiment, nose portion 504 and rear portion 506 can be left open to accommodate a tapered delivery shaft of an introducer that can extend all the way through the device 500.

Drive screws 518 can be inserted through guide apertures 520 in rear portion 506 and through expansion blocks 514. Actuation of drive screws 518, such as by an introducer as described herein, drives blocks 514 closer together, which causes deflection of the flexure members 512, resulting in expansion of the structural members 510 and distraction of the end plates 508. In one embodiment, blocks 514b in FIGS. 13A-13C can be tapped to accommodate drive screws 518 and blocks 514a can provide a clearance fit with screws 518. When drive screws 518 are actuated, this allows blocks 514a to be pulled towards blocks 514b, causing the device 500 to distract. Similarly, blocks 514a and 514c in FIGS. 14A-14B can be tapped and blocks 514b can provide a clearance fit. In such a configuration, the opposite end from the hex of screws 518 can have a shoulder to draw block 514b towards blocks 514c and 514a. In some embodiments, mechanisms other than drive screws can be used to distract device. Such mechanisms include, for example, a pop-rivet mechanism, a sardine key and ribbon, a tourniquet and wire, a saw blade/ratchet, and shape changing materials such as a shape memory alloy or a conducting polymer actuator. The rear block can include a projection for engaging the teeth of the drive mechanism. In one embodiment, piezo-electric inch-worm motors can be used to actuate the movement of blocks 514. In another embodiment, a balloon can be inserted into device and inflated to expand the device. The balloon can remain in the device and function like the nucleus of a disc.

In various embodiments, device body 502 is shaped to be ergonomic. Device body 502 can have various shapes, such as, for example, rectangular, kidney, or football shaped. A kidney or football shaped device body 502 maximizes contact between the device and the vertebral bodies because the end plates of vertebrae tend to be slightly concave. One or both ends of the device may also be tapered in order to facilitate insertion. This minimizes the amount of force needed to initially insert the device and separate the vertebral bodies. In addition, the device may be convex along both its length and its width, or bi-convex. Device 500 can be constructed in various sizes depending on the type of vertebra and size of patient with which it is being used.

Device body 502 can also be comprised of various materials. In one embodiment, device is comprised of a ductile material. Such materials can include, for example, titanium, nitinol, and thermoplastics. In some embodiments, the material near the ends of the flexures 512 can be cold-worked to increase the stiffness of the device as it distracts. Heat treating could also be used to alleviate machining stresses and could be followed by hardening treatment to make the device stiffer. Additionally, in some embodiments the flexures can be affixed to the device in subsequent manufacturing steps in order to permit the flexures to be made from a different material or materials, or materials treated differently, than the structural members and end plates of the device. Flexures could also be laminated beams having a core of another stiff material, a soft material such as a foam, or an open core. Having a soft or open core would allow the flexures to effectively decrease in thickness as they are bent around the curved surfaces of the struts. This would decrease the amount of strain present in the flexure due to bending, allowing the device to accommodate greater functional loading.

Device 500 can be inserted with tapered nose portion 504 first. In one embodiment, a working channel of 8-26 mm is required for insertion of the device. One device 500 can be inserted, or, for additional support, two devices 500 can be inserted. Two devices 500 can be especially useful for treating larger patients in which the device may encounter higher loads. In another embodiment, three or more small devices can be inserted into the disc space in order to very accurately control the orientation and distance between discs. Three or more distraction mechanisms may be positioned circumferentially between two circular endplates to result in very accurate control and orientation of the end plates. Such a device would resemble a hexapod. In another embodiment, two or more devices may be mated or assembled in the disc space to work congruently in performing distraction either in height or width.

Once inserted in the disc space, an insertion tool or introducer as described herein can be actuated to rotate drive screws 518. Drive screws 518 can be actuated from the rear of device 500 to allow insertion tool to reposition or, if necessary, remove device 500 prior to disengaging from device 500. Drive screws 518 can be actuated the same amount for uniform distraction on both sides of an embodiment with two drive screws or may be actuated different amounts for non-uniform distraction with one side of the device 500 higher than the other. Non-uniform distraction causes torsional forces on flexures. Alternatively, an embodiment can be driven with a single flexure and single drive screw or with multiple flexures multiplexed to a single drive screw arrangement.

Unlike many common scissor jacks, such as, for example, car jacks, device 500 can easily be distracted from its lowest, or most compressed, state. This is because the flexure members 512 on each end of a given structural member are oriented such that the tensile loads on the flexures do not act towards each other, but instead pass by each other, like passing cars (see arrow A and arrow B in FIG. 13B). Common jacks, which do not utilize flexure members, may have difficulty distracting from the lowest state because the tensile loads can act "heads on" with each other, putting the device under strong internal horizontal compression but without a significant force component in the vertical direction at the lowest state that can easily initiate distraction. The tension in the flexure member required to support a compressive load is equal to the compressive load multiplied by the cosine of the angle of the rigid link divided by the sine of the rigid link. Because the sine of zero degrees, the angular position of normal scissor jacks in the compressed state, is equal to zero, the force required for initial distraction can be effectively very large. The rigid links of the device of various embodiments of the present invention may start off in the position of zero angular position, but because the flexure members are on opposing sides of the rigid links the effective angular position is non-zero, making the force required for initial distraction finite and generally smaller than a conventional scissor jack.

Figure 17D:
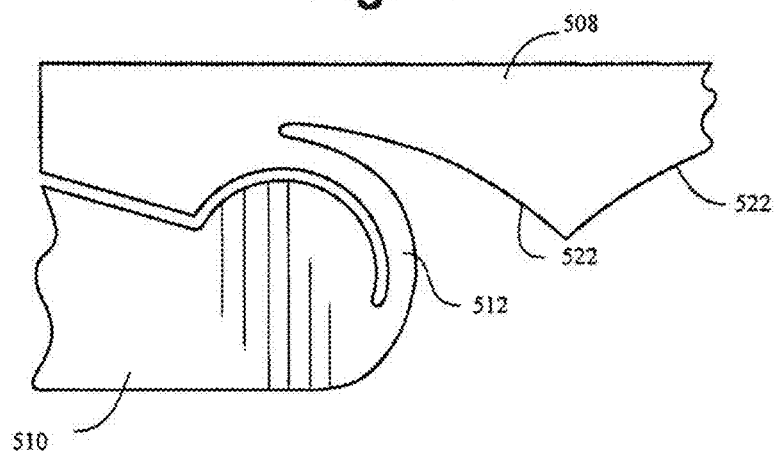
FIG. 17D is a partial view of a portion of an embodiment of a distractible intervertebral body fusion device according to an aspect of the present invention.

As drive screws 518 are actuated, the device 500 is distracted as shown in FIGS. 15 and 16. Drive screws 518 (not shown in FIGS. 15 and 16) drive expansion blocks 514 together, which cause flexure members 512 to deflect thereby expanding structural members 510 to distract end plates 508. Referring now to FIGS. 17A-17D, FIGS. 17A and 17D depict a flexure member 512 and structural member 510 before distraction, whereas FIGS. 17B and 17C depict after distraction. Each flexure member 512 begins wrapped around the curved end of the structural member 510. Note in FIG. 17A that the flexure 512 rests on the structural member 510. This allows the device 500 to carry a large compressive load in the compressed state without greatly deforming the flexure 512. As the structural members 510 are distracted, the flexure members 512 bend towards flat. In this embodiment, the flexure members 512 do not bend all the way flat, however, even at maximum distraction of the end plates 508, because they contact curved backstop 522. This allows the device 500 to carry a large compressive load in the distracted state without further deforming the flexure 512. Curved backstop 522 has a "frowning eyebrows" configuration in order to provide opposed curved surfaces for opposing flexure members 512. Because the flexure members 512 do not have to bend until they are completely flat to reach complete distraction, the amount of strain on the flexure members 512 necessary for complete distraction is minimized. The likelihood of device failure is therefore reduced.

Figure 17E:
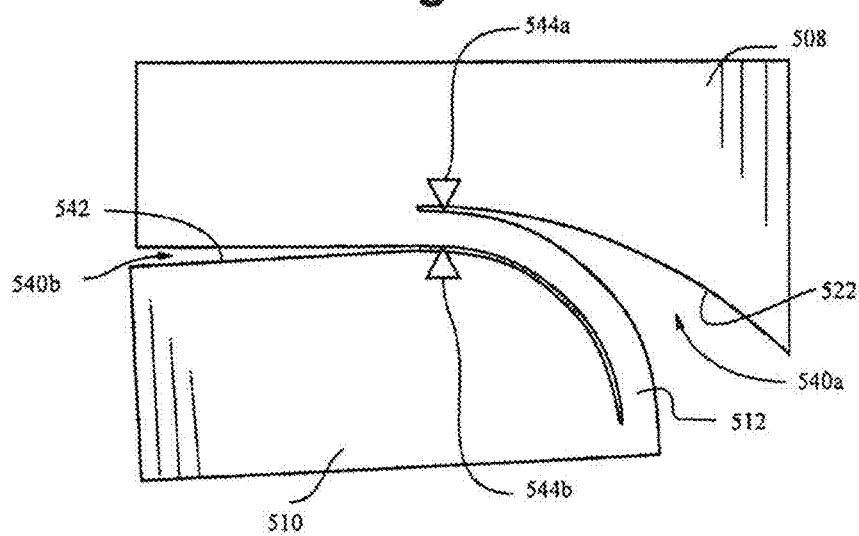
FIG. 17E is a partial view of a portion of an embodiment of a distractible intervertebral body fusion device according to an aspect of the present invention.

FIGS. 17E-17G depict the behavior of flexures as the device is distracted. Flexure member 512 defines a first open area, or kerf 540a, between curved backstop 522 and flexure member 512 and a second kerf 540b between inner perimeter 542 of structural member 510 and flexure member 512. When device 500 is in a collapsed configuration (FIG. 17E), kerf 540a is wider than kerf 540b. As device distracts, flexure member 512 flattens out towards curved backstop 522, so kerf 540b widens as kerf 540a narrows. The fulcrum around which flexure member 512 bends is shown by arrows 544a and 544b. As can be seen in FIGS. 17E-17G, the fulcrum 544a, 544b translates along the flexure member 512 as it bends. Fulcrum 544a, 544b therefore travels in both vertical and horizontal directions. This provides for increased distraction of the device. As the fulcrum 544a, 544b moves along the flexure member 512 as the device distracts, a greater portion of the compressive load on the device 500 is supported by the structural member 510 and, accordingly, the tensile forces on the flexure member 512 are reduced. The device 500 of this embodiment is therefore strongest when it is fully distracted.

In various embodiments, distractible intervertebral body fusion device has a one-piece device body that can be manufactured in a distracted or partially distracted state. This provides great cost savings over devices that require multiple pieces to be separately manufactured and assembled. Manufacturing in the distracted state provides additional clearance for assembly and for access by manufacturing tools, the size of which is inversely proportional to the cost of manufacturing. In addition, when the device is manufactured in the distracted state, the device can be compressed into a position of minimal height while compressive stress remains in the flexure members. This compressive stress results in a negative mean stress, which can extend the fatigue life of the device. In one embodiment, the device can be manufactured using wire or sink edm. In another embodiment, the device can be manufactured using three-dimensional printing techniques or the like. In some embodiments, portions of the flexures can be machined separately and welded to the device. This allows for flexures that have zero kerf and rest completely against the backstops once distracted.

In one embodiment, the surface of the device can be treated to minimize surface roughness or to reduce pitting of the material within the body. A rough surface or pits can increase the stress on the device, which can result in shortening of the fatigue life and/or reduce fatigue strength. In one embodiment, the surface can be treated with electro-polishing. In another embodiment, the surface can be left untreated because a rough surface on the end plates helps prevent accidental extrusion of the device. In one embodiment, the device can also be coated with a highly elastic, impermeable material to extend its fatigue life. Specifically, the impermeable material would prevent the corrosive properties of blood from degrading the device. In another embodiment, the device can be comprised of a biocompatible material, so that no coating is necessary. In a further embodiment, the device can be made of a biodegradable material designed to degrade in the body at a selected stage of the healing process, such as after bone fusion.

Numerous other types of supports may be used with the device. Supports can be used to supplement the compressive strength, bending, or torsional strength of device. In one embodiment, one or more rigid supports can be inserted into the open space between end plates after distraction to help keep the end plates in their distracted state. In another embodiment, chocks can be placed at the intersection of structural members in each strut to provide further support for struts. In a further embodiment, a rod and screws can be used with the device as part of an assembly affixed to the vertebral body.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. An inserter for inserting and expanding a distractible intervertebral body fusion device into an intervertebral disc space defined between adjacent vertebrae of a patient, comprising:
    a shaft frame having a proximal end and a distal end;
    a drive shaft assembly extending from the distal end of the shaft frame, the drive shaft assembly adapted to be attached to a distractible intervertebral body fusion device such that rotation of the drive shaft assembly causes the device to expand between a compressed configuration and an expanded configuration;
    a support shaft assembly extending from the distal end of the shaft frame adjacent the drive shaft assembly, the support shaft assembly adapted to be attached to the distractible intervertebral body fusion device to stabilize the device as the drive shaft assembly is rotated to expand the device; and
    a drive housing operably connected to the shaft frame and extending outwardly from the shaft frame and non-coaxially with the drive shaft assembly, the drive housing extending from the shaft frame at a location between the distal end and the proximal end of the shaft frame, the drive housing providing access into the shaft frame to a proximal end of the drive shaft assembly.

2. The inserter of claim 1, further comprising an actuation tool disposed within the drive housing, the actuation tool extending through the access into the shaft frame to interface with the proximal end of the drive shaft assembly.

3. The inserter of claim 2, wherein the proximal end of the drive shaft assembly comprises a shaft gear and a distal end of the actuation tool includes a drive gear that meshes with the shaft gear, and wherein activation of the actuation tool causes a rotation of the drive gear that thereby causes a rotation of the shaft gear to rotate the drive shaft assembly.

4. The inserter of claim 2, wherein the actuation tool is an electric screw driver.

5. The inserter of claim 1, wherein the drive shaft assembly includes a joint extending from the distal end of the shaft frame and a drive link extending distally from the joint.

6. The inserter of claim 5, wherein one of the joint and the drive link includes a slot to which the other of the joint and the drive link is connected with a pin, the slot allowing relative longitudinal movement of the joint and the drive link.

7. The inserter of claim 6, further comprising a biasing member disposed on one of the joint and the drive link, the biasing member biasing the relative longitudinal movement of the joint and the drive link.

8. The inserter of claim 1, further comprising a device interface positioned adjacent a distal end of the drive shaft assembly and a distal end of the support shaft assembly, the device interface including a pair of apertures, one of the drive shaft assembly and the support shaft assembly extending through each aperture.

9. The inserter of claim 8, wherein the device interface has a distal surface at least a portion of which is shaped to conform to an outer surface of a particular distractible intervertebral body fusion device for insertion into the disc space.

10. The inserter of claim 1, wherein the shaft frame includes markings indicating a height of a distractible intervertebral body fusion device that is distracted by rotation of the drive shaft assembly.

11. The inserter of claim 10, wherein the shaft frame includes a longitudinal slot along which the height markings are located, and further comprising a block stop selectively positionable along the slot, the block stop preventing further rotation of the drive shaft assembly when the distractible intervertebral body fusion device has reached the height indicated by the marking at which the block stop is located.

12. An inserter for inserting and expanding a distractible intervertebral body fusion device into an intervertebral disc space defined between adjacent vertebrae of a patient, comprising:
a shaft frame having a proximal end and a distal end;
means for expanding a distractible intervertebral body fusion device between a compressed configuration and an expanded configuration extending from the distal end of the shaft frame;
means for stabilizing the distractible intervertebral body fusion device as the means for expanding is used to expand the device, the means for stabilizing extending from the distal end of the shaft frame adjacent the means for expanding; and
a drive housing operably connected to the shaft frame and extending outwardly from the shaft frame and non-coaxially with the means for expanding, the drive housing extending from the shaft frame at a location between the distal end and the proximal end of the shaft frame, the drive housing providing access into the shaft frame to a proximal end of the means for expanding.

13. The inserter of claim 12, further comprising means for rotating the means for expanding disposed within the drive housing, the means for rotating extending through the access into the shaft frame to interface with the proximal end of the means for expanding.

14. The inserter of claim 13, wherein a distal end of the means for rotating includes a drive gear that engages the proximal end of the means for expanding, and wherein activation of the means for rotating causes a rotation of the drive gear that thereby causes a rotation of the means for expanding.

15. The inserter of claim 12, further comprising a device interface positioned adjacent a distal end of the means for expanding and a distal end of the means for stabilizing, the device interface including a pair of apertures, one of the means for expanding and the means for stabilizing extending through each aperture.

16. The inserter of claim 15, wherein the device interface has a distal surface at least a portion of which is shaped to conform to an outer surface of a particular distractible intervertebral body fusion device for insertion into the disc space.

17. The inserter of claim 12, wherein the shaft frame includes means for indicating a height of a distractible intervertebral body fusion device that is expanded by the means for expanding.

18. The inserter of claim 17, wherein the shaft frame further comprises a means for preventing further expansion of the device beyond a predetermined maximum height indicated by the means for indicating.

19. A method comprising:
providing a distractible intervertebral body fusion device, the device expandable between a compressed configuration and an expanded configuration;
providing an inserter having a shaft frame with a distal end and a proximal end, a drive shaft assembly extending from the distal end of the shaft frame, a support shaft assembly extending from the distal end of the shaft frame, and a drive housing operably connected to the shaft frame and extending outwardly from the shaft frame distally of the proximal end of the shaft frame, the drive housing providing access into the shaft frame to a proximal end of the drive shaft assembly;
providing an actuation tool; and
providing instructions for implanting the distractible intervertebral body fusion device into a disc space provided between adjacent vertebrae of a patient with the inserter and actuation tool, the instructions comprising:
inserting the actuation tool into the drive housing such that the actuation tool interfaces with the proximal end of the drive shaft assembly;
attaching a distal end of the drive shaft assembly to the distractible intervertebral body fusion device;
attaching a distal end of the support shaft assembly to the distractible intervertebral body fusion device;
inserting the distractible intervertebral body fusion device into the disc space with the inserter; and
activating the actuation tool to rotate the drive shaft assembly to expand the distractible intervertebral body fusion device from the compressed configuration to the expanded configuration.

20. The method of claim 19, wherein the step of interfacing the actuation tool with the proximal end of the drive shaft assembly includes interfacing a drive gear at a distal end of the actuation tool with a shaft gear at the proximal end of the drive shaft assembly, and wherein the step of activating the actuation tool to rotate the drive shaft assembly includes rotating the drive gear to cause a rotation of the shaft gear.

21. The method of claim 19, wherein the step of providing an actuation tool includes providing an electric screwdriver.

22. The method of claim 19, further comprising providing a plurality of device interfaces, the plurality of device interfaces having more than one different configuration with each device interface having a distal surface at least partially shaped to conform to an outer surface of a particular type of intervertebral body fusion device, and wherein the instructions further comprise:
selecting a device interface from the plurality of device interfaces with a configuration shaped to conform to a type of intervertebral body fusion device of the provided intervertebral body fusion device; and
attaching the device interface to the drive shaft assembly and support shaft assembly adjacent the distal ends of the drive shaft assembly and support shaft assembly, and wherein the steps of attaching the drive shaft assembly and support shaft assembly to the intervertebral body fusion device include interfacing the distal surface of the device interface with the intervertebral body fusion device.

23. The method of claim 19, wherein the shaft frame includes a longitudinal slot and markings along the slot indicating a height of the distractible intervertebral body fusion device as it is expanded by the inserter and the inserter includes a block stop selectively positionable along the slot, and wherein the instructions further comprise:
sliding the block stop along the slot and fixing the block stop in place at a maximum desired expanded height of the intervertebral body fusion device, and
the step of activating the actuation tool to rotate the drive shaft assembly to expand the distractible intervertebral body fusion device from the compressed configuration to the expanded configuration includes activating the actuation tool until the block stop prevents further rotation of the drive shaft.

24. The method of claim 20, wherein the step of inserting the distractible intervertebral body fusion device into the disc space includes striking the proximal end of the shaft frame with a hammer or mallet.

* * * * *